US012594198B2

(12) United States Patent
Nagano

(10) Patent No.: US 12,594,198 B2
(45) Date of Patent: Apr. 7, 2026

(54) DISPOSABLE WEARING ARTICLE AND METHOD FOR MANUFACTURING THE SAME

(71) Applicant: DAIO PAPER CORPORATION, Ehime (JP)

(72) Inventor: Akiko Nagano, Ehime (JP)

(73) Assignee: Daio Paper Corporation, Ehime (JP)

( * ) Notice: Subject to any disclaimer, the term of this patent is extended or adjusted under 35 U.S.C. 154(b) by 243 days.

(21) Appl. No.: 18/267,600

(22) PCT Filed: Feb. 15, 2022

(86) PCT No.: PCT/JP2022/005958
§ 371 (c)(1),
(2) Date: Jun. 15, 2023

(87) PCT Pub. No.: WO2022/201974
PCT Pub. Date: Sep. 29, 2022

(65) Prior Publication Data
US 2024/0099907 A1     Mar. 28, 2024

(30) Foreign Application Priority Data
Mar. 23, 2021    (JP) ................................. 2021-048148

(51) Int. Cl.
*A61F 13/511* (2006.01)
*A61F 13/15* (2006.01)
*A61L 15/20* (2006.01)

(52) U.S. Cl.
CPC .. *A61F 13/51113* (2013.01); *A61F 13/15731* (2013.01); *A61L 15/20* (2013.01);
(Continued)

(58) Field of Classification Search
CPC .............. A61F 13/51113; A61F 13/512; A61F 13/5126; A61F 13/8405;
(Continued)

(56) References Cited

U.S. PATENT DOCUMENTS 6,166,285 A     12/2000  Schulte
8,138,387 B2 *   3/2012  Vega ....................... A61L 15/16
                                                             604/385.24
(Continued)

FOREIGN PATENT DOCUMENTS

EP          4159173 A1     4/2023
EP          4190290 A1     6/2023
(Continued)

OTHER PUBLICATIONS

Extended European Search Report for EP Patent Application No. 22774774.8, dated Feb. 11, 2025.
(Continued)

*Primary Examiner* — Catharine L Anderson
(74) *Attorney, Agent, or Firm* — Andrus Intellectual Property Law, LLP

(57)          ABSTRACT

A disposable wearing article having an excellent rash preventing effect. A skin contact region in a top sheet formed of a nonwoven fabric having a basis weight of 5 to 40 g/m2 has a glycerin-containing region in which glycerin is applied in a region to which a body fluid pervious treatment agent containing a nonionic surfactant having an amide and/or amino group is applied.

3 Claims, 16 Drawing Sheets

(52) U.S. Cl.
CPC .............. *A61F 2013/15406* (2013.01); *A61F 2013/51117* (2013.01)

(58) Field of Classification Search
CPC .. A61F 2013/51059; A61F 2013/51066; A61F 2013/51073; A61F 2013/51117; A61F 2013/5127; A61F 2013/5128; A61F 2013/8455; A61F 2013/8461
See application file for complete search history.

(56) References Cited

U.S. PATENT DOCUMENTS

| | | | |
|---|---|---|---|
| 8,481,480 B1 * | 7/2013 | Lam | A61K 8/898 514/642 |
| 10,517,982 B2 * | 12/2019 | Vega | A61L 15/26 |
| 2004/0158216 A1 * | 8/2004 | Kasai | A61F 13/8405 604/367 |
| 2005/0059941 A1 * | 3/2005 | Baldwin | A61L 15/20 604/367 |
| 2008/0249491 A1 | 10/2008 | Young | |
| 2008/0287903 A1 | 11/2008 | Vega et al. | |
| 2021/0059873 A1 | 3/2021 | Fujikawa | |
| 2023/0218450 A1 * | 7/2023 | Nakamura | A61F 13/51113 604/367 |

FOREIGN PATENT DOCUMENTS

| | | | | |
|---|---|---|---|---|
| JP | 2003-527147 | | 9/2003 | |
| JP | 2004166832 A | | 6/2004 | |
| JP | 2006-346211 | | 12/2006 | |
| JP | 2010-526630 | | 8/2010 | |
| JP | 2013-059517 | | 4/2013 | |
| JP | 2018-178331 | | 11/2018 | |
| JP | 2019-002122 | | 1/2019 | |
| JP | 2020174996 A | | 10/2020 | |
| JP | 6911090 B2 * | | 7/2021 | .......... A61F 13/476 |
| WO | 2013038965 A1 | | 3/2013 | |
| WO | 2020044968 A1 | | 3/2020 | |

OTHER PUBLICATIONS

International Search Report and the Written Opinion for PCT/JP2022/005958, dated Apr. 26, 2022.

* cited by examiner (a)

(b)

(c)

(a)

(b)

(c)

(d)

(e)

(f)

(a)

(b)

(c)

(d)

(a)

(b)

DISPOSABLE WEARING ARTICLE AND METHOD FOR MANUFACTURING THE SAME

CROSS-REFERENCE TO RELATED APPLICATIONS

This application is the U.S. national stage application of International Application PCT/JP2022/005958, filed Feb. 15, 2022, which international application was published on Sep. 29, 2022, as International Publication WO 2022/201974 in the Japanese language. The International Application claims priority of Japanese Patent Application No. 2021-048148, filed Mar. 23, 2021. The international application and Japanese application are both incorporated herein by reference, in entirety.

TECHNICAL FIELD

The present invention relates to a disposable wearing article such as a disposable diaper or a sanitary napkin, and a method for manufacturing the same.

BACKGROUND ART

A disposable wearing article, particularly a disposable diaper often causes roughness of a skin of a wearer, particularly, rash disadvantageously. A factor for this is, for example, deterioration of a skin barrier function due to physical stimulation (friction and hardness) to the skin of the wearer or skin dryness.

It is also known to apply a hydrophilic lotion to a top sheet formed of a nonwoven fabric in order to reduce friction and the like (see Patent Literature 1). The hydrophilic lotion is preferable because the hydrophilic lotion can prevent hardness of a waxy substance or deterioration of a liquid pervious property. In particular, a hydrophilic lotion containing water is preferred in order to prevent skin dryness.

However, there is still room for improvement in suppressing diaper rash. For example, since a skin of an infant is sensitive, in a diaper worn by the infant, so-called diaper rash easily occurs.

CITATION LIST

Patent Literature

Patent Literature 1: JP 2010-526630 A
Patent Literature 2: JP 2018-178331 A

SUMMARY OF INVENTION

Technical Problem

Therefore, a main object of the present invention is to provide a disposable wearing article having an excellent rash preventing effect and a method for manufacturing the same.

Solution to Problem

A disposable wearing article that has solved the above problem includes
a top sheet having a skin contact region in contact with a skin of a wearer,
wherein the top sheet is formed of a nonwoven fabric having a basis weight of 5 to 40 g/m², and
the skin contact region has,
in a region to which a body fluid pervious treatment agent containing a nonionic surfactant having an amide and/or amino group is applied,
a glycerin-containing region to which glycerin is applied.
A method for manufacturing a disposable wearing article including a top sheet having a skin contact region in contact with a skin of a wearer, including:
using a nonwoven fabric having a basis weight of 5 to 40 g/m² as the top sheet; and
applying glycerin
to a region to which a body fluid pervious treatment agent containing a nonionic surfactant having an amide and/or amino group is applied in the nonwoven fabric.

Advantageous Effects of Invention

According to the present invention, a body fluid pervious property improving effect by a nonionic surfactant and a rash preventing effect by glycerin are combined to provide an advantage such as an excellent rash preventing effect.

DESCRIPTION OF EMBODIMENTS

Figure 1:
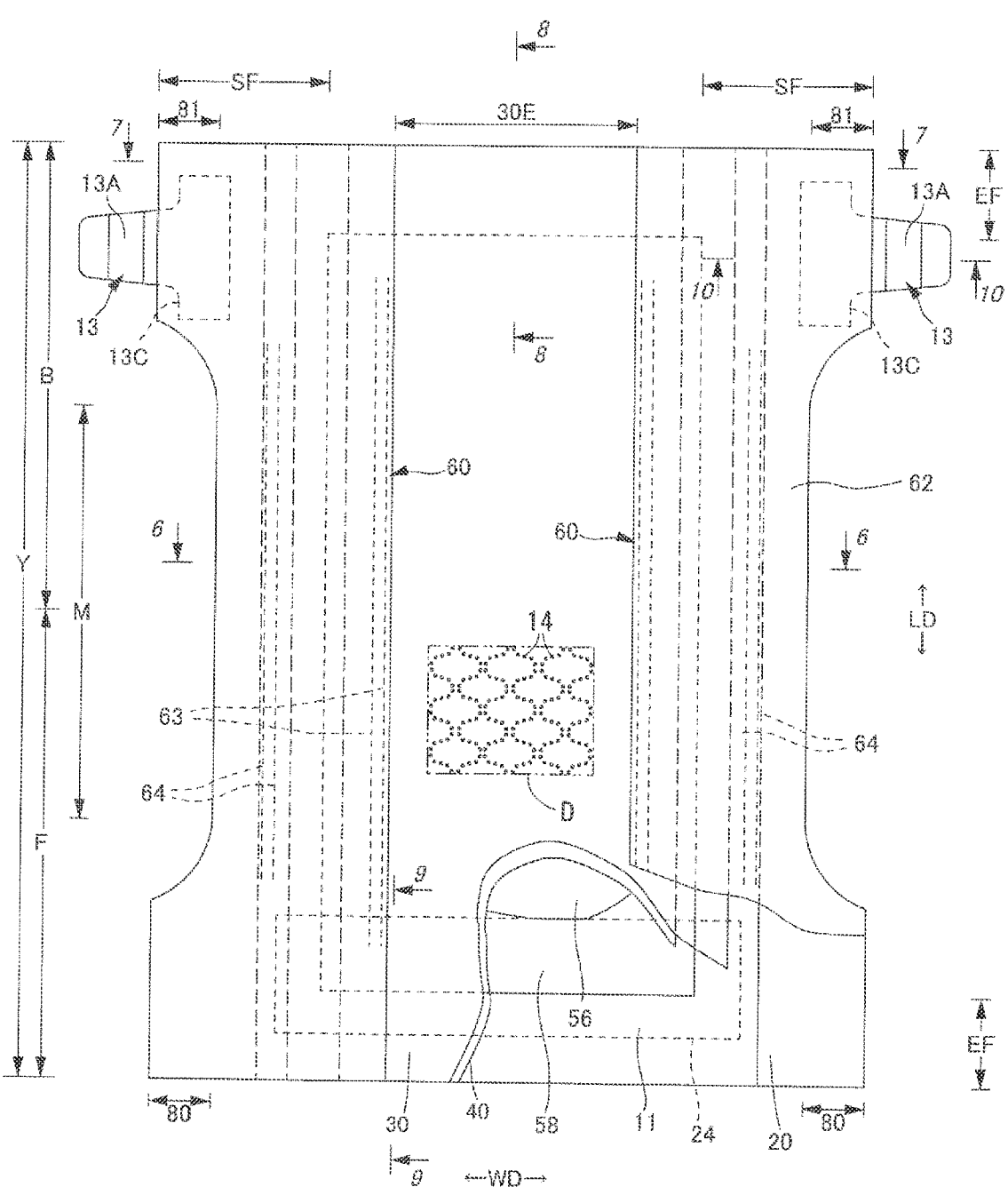
FIG. 1 is a plan view illustrating an inner surface of a tape-type disposable diaper in an unfolded state.

A disposable wearing article according to the present invention includes a disposable diaper, a sanitary napkin, and the like.
Hereinafter, an embodiment of the present invention will be described.

FIGS. 1 to 5 illustrate a tape-type disposable diaper as an example of the disposable wearing article. In the drawings, a reference character X indicates the maximum width of the diaper excluding a connecting tape, and a reference character L indicates the maximum length of the diaper. A dotted pattern portion in a cross-sectional view indicates an adhesive as a bonding means for bonding constituent members. A hot melt adhesive can be applied by a known method such as slot application, bead application into a continuous line or a dot shape, spray application into a spiral shape, a Z shape, or a wave shape, or pattern coating (transfer of a hot melt adhesive by a letterpress method). Alternatively or in addition, in a fixed portion of an elastic member, the hot melt adhesive can be applied to an outer peripheral surface of the elastic member, and the elastic member can be fixed to an adjacent member. Examples of the hot melt adhesive include an EVA-based agent, a pressure sensitive adhesive rubber-based agent (elastomer-based agent), a polyolefin-based agent, and a polyester/polyamide-based agent, and these can be used without particular limitation. As the bonding means for bonding constituent members, a means by material welding such as heat sealing or ultrasonic sealing can also be used.

As a nonwoven fabric in the following description, a known nonwoven fabric can be appropriately used according to a site or a purpose. Examples of a constituent fiber of the nonwoven fabric include, but are not limited to, a synthetic fiber such as a polyolefin-based fiber including polyethylene and polypropylene, a polyester-based fiber, or a polyamide-based fiber (including a composite fiber such as core-sheath in addition to a single component fiber), a regenerated fiber such as rayon or cupra, and a natural fiber such as cotton. These fibers can be mixed and used. In order to enhance flexibility of the nonwoven fabric, it is preferable to use a crimped fiber as the constituent fiber. In addition, the constituent fiber of the nonwoven fabric may be a hydrophilic fiber (including a fiber that has become hydrophilic by a hydrophilizing agent), a hydrophobic fiber, or a water-repellent fiber (including a fiber that has become water-repellent by a water repellent agent). The nonwoven fabric is generally classified into a short fiber nonwoven fabric, a long fiber nonwoven fabric, a spunbonded nonwoven fabric, a meltblown nonwoven fabric, a spunlace nonwoven fabric, a thermal bond (air through) nonwoven fabric, a needle punch nonwoven fabric, a point bond nonwoven fabric, a stacked nonwoven fabric an (in addition to an SSS nonwoven fabric in which the same or similar nonwoven fabric layers are stacked, an SMS nonwoven fabric, an SMMS nonwoven fabric, or the like in which different nonwoven fabric layers are stacked and a meltblown layer is sandwiched between spunbond layers), and the like depending on a fiber length, a sheet forming method, a fiber bonding method, and a stacked structure, and any of these nonwoven fabrics can be used. The stacked nonwoven fabric means one that is manufactured as an integrated nonwoven fabric including all the layers and has been subjected to fiber bonding processing over all the layers, and does not include one obtained by bonding a plurality of separately manufactured nonwoven fabrics to each other by a bonding means such as a hot melt adhesive.

The present tape-type disposable diaper includes a ventral side portion F extending forward from the center in the front-back direction LD, and a dorsal side portion B extending backward from the center in the front-back direction LD. In addition, the present tape-type disposable diaper has a shape including a crotch portion M extending from the front side of the center in the front-back direction of the product to the back side of the center in the front-back direction of the product, front wings 80 protruding to both the left and right sides at positions away in the front side of the center in the front-back direction of the product, and back wings 81 protruding to both the left and right sides at positions away in the back side of the center in the front-back direction of the product. Furthermore, the present tape-type disposable diaper includes an absorber 56 incorporated in a range including the crotch portion, a liquid pervious top sheet 30 covering a front surface side of the absorber 56, a liquid impervious sheet 11 covering a back surface side of the absorber 56, and an exterior nonwoven fabric 12 covering a back surface side of the liquid impervious sheet 11 and forming a product outer surface.

Hereinafter, a material of each portion and a characteristic part thereof will be described sequentially.

(Absorber)

The absorber 56 absorbs and holds an excrement liquid, and can be formed by an assembly of fibers. As this fiber assembly, in addition to those obtained by accumulating a short fiber such as fluff pulp or a synthetic fiber, a filament assembly obtained by opening a tow (fiber bundle) of a synthetic fiber such as cellulose acetate as necessary can also be used. In a case where fluff pulp or a short fiber is accumulated, a fiber basis weight may be, for example, about 100 to 300 $g/m^2$. In a case of a filament assembly, a fiber basis weight may be, for example, about 30 to 120 $g/m^2$. In a case of a synthetic fiber, a fineness is, for example, 1 to 16 dtex, preferably 1 to 10 dtex, and more preferably 1 to 5 dtex.

The planar shape of the absorber 56 can be determined appropriately, and can be a rectangular shape or a shape that is narrowing such that the middle of the absorber 56 in the front-back direction LD is along a periphery of a leg.

(Super Absorbent Polymer Particles)

The absorber 56 may contain super absorbent polymer particles partially or entirely. The super absorbent polymer particles include "powder" in addition to "particles". As the super absorbent polymer particles, those used for this type of absorbent article can be used as they are. The particle diameters of the super absorbent polymer particles are not particularly limited. However, for example, when sieving using a standard sieve of 500 μm (JIS Z8801-1: 2006) (shake for five minutes) is performed, and particles falling under the sieve using this sieving are sieved using a standard sieve of 180 μm (JIS Z8801-1: 2006) (shake for five minutes), it is desirable that a ratio of particles remaining on the standard sieve of 500 μm is 30% by weight or less, and a ratio of particles remaining on the standard sieve of 180 μm is 60% by weight or more.

A material of the super absorbent polymer particles can be used without particular limitation, but those having a water absorption capacity of 40 g/g or more are suitable. Examples of the super absorbent polymer particles include a starch-based material, a cellulose-based material, and a synthetic polymer-based material. A starch-acrylic acid (salt) graft copolymer, a saponified product of a starch-acrylonitrile copolymer, a cross-linked product of sodium carboxymethyl cellulose, an acrylic acid (salt) polymer, or the like can be used. As the shapes of the super absorbent polymer particles, a usually used particulate material shape is suitable, but other shapes can also be used.

As the super absorbent polymer particles, those having a water absorption speed of 70 seconds or less, particularly 40 seconds or less are suitably used. When the absorption speed is too slow, so-called returning that liquid supplied into the absorber 56 returns out of the absorber 56 tends to occur.

As the super absorbent polymer particles, those having a gel strength of 1000 Pa or more are suitably used. This makes it possible to effectively suppress a sticky feeling after liquid absorption even in a case of using the bulky absorber 56.

The basis weight of the super absorbent polymer particles can be appropriately determined depending on the absorption amount required for an application of the absorber 56. Therefore, the basis weight can be usually 50 to 350 g/m² although this cannot be applied generally.

(Wrapping Sheet)

The absorber 56 can be incorporated as an absorbent element 50 wrapped in a wrapping sheet 58 in order to prevent escape of the super absorbent polymer particles or to improve shape maintenance of the absorber 56. As the wrapping sheet 58, tissue paper, particularly crepe paper, a nonwoven fabric, a polylaminated nonwoven fabric, a sheet with small holes, and the like can be used. Note that it is desirable that the wrapping sheet 58 is a sheet from which super absorbent polymer particles do not escape. When a nonwoven fabric is used instead of crepe paper, a hydrophilic spunbonded/melt blown/melt blown/spunbonded (SMMS) nonwoven fabric is particularly suitable, and polypropylene, polyethylene/polypropylene, or the like can be used as a material thereof. A nonwoven fabric having a fiber basis weight of 5 to 40 g/m², particularly of 10 to 30 g/m² is desirable.

Figure 3:
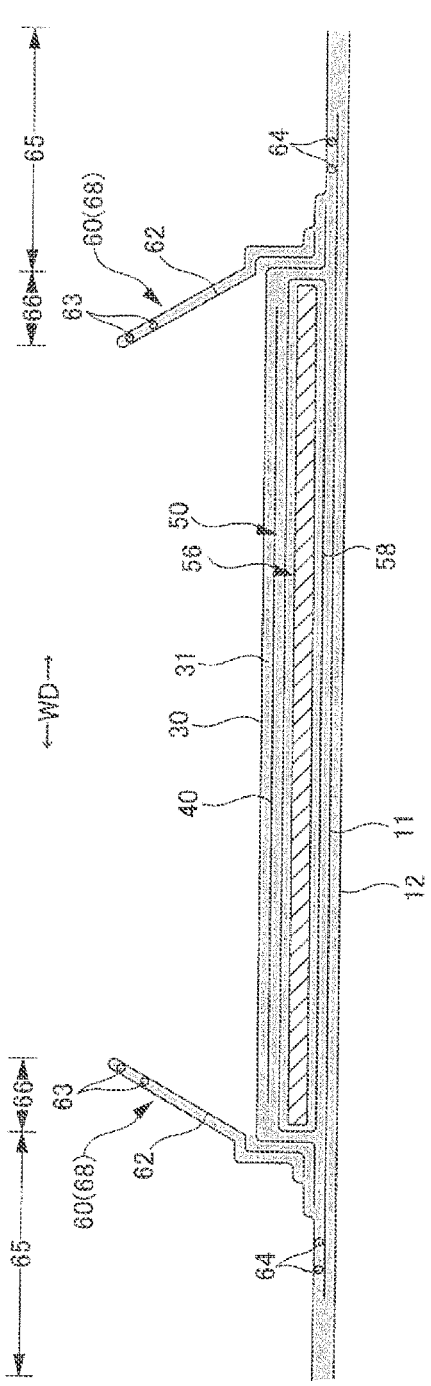
FIG. 3 is a cross-sectional view cut along line 6-6 of FIG. 1.
Figure 4:
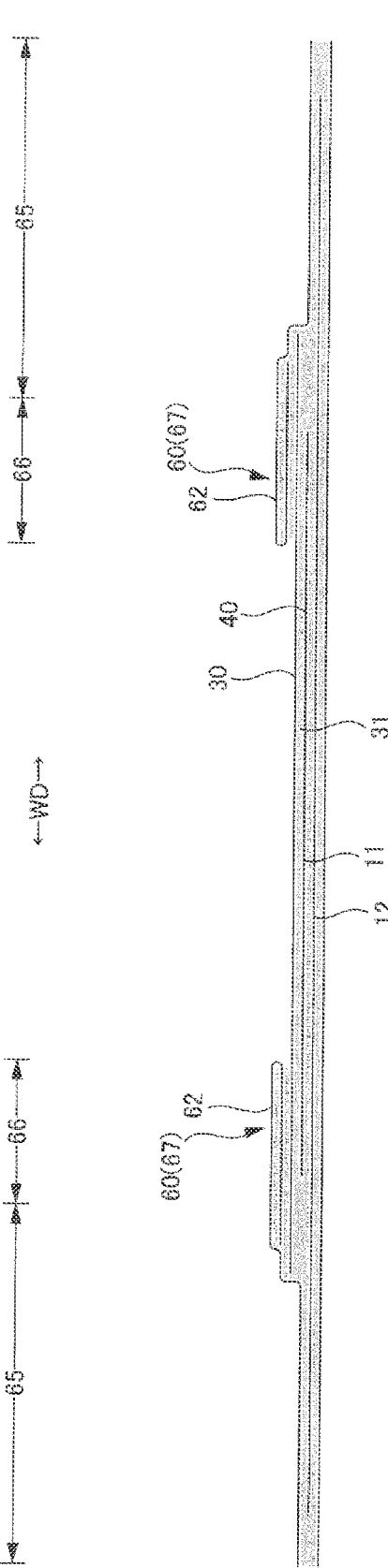
FIG. 4 is a cross-sectional view cut along line 7-7 of FIG. 1.
Figure 5:
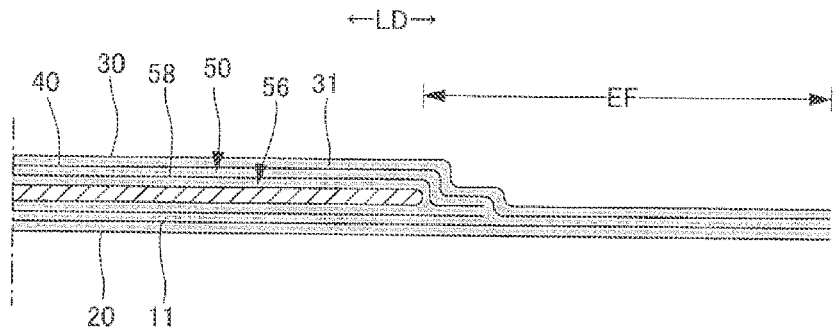
FIG. 5(a) is a cross-sectional view cut along line 8-8 of FIG. 1.
FIG. 5(b) is a cross-sectional view cut along line 9-9 of FIG. 1.
FIG. 5(c) is a cross-sectional view cut along line 10-10 of FIG. 1.
Figure 5:
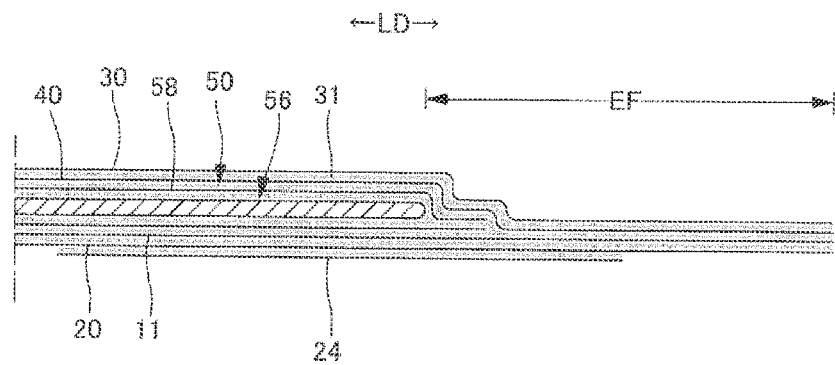
Figure 5:
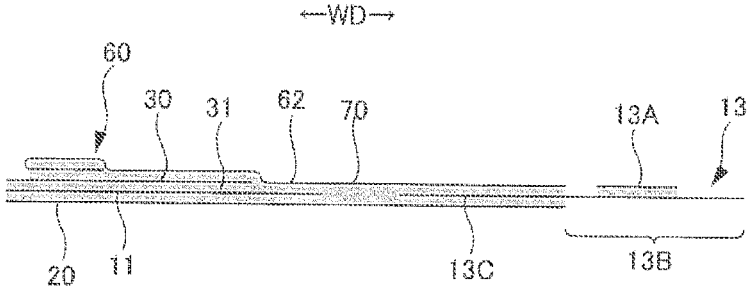

As illustrated in FIG. 3, the single wrapping sheet 58 may wrap the whole of the absorber 56, or a plurality of the wrapping sheets 58 such as upper and lower two wrapping sheets 58 may wrap the whole of the absorber 56. The wrapping sheet 58 can also be omitted.

(Top Sheet)

The top sheet 30 extends from a front end to a back end of the product in the front-back direction and extends to a lateral side more than the absorber 56 in the width direction WD. For example, when a starting point of a rising gather 60 described later is located closer to the center in the width direction WD than a side edge of the absorber 56, appropriate deformation can be made, for example, the width of the top sheet 30 is made shorter than the maximum width of the absorber 56 as necessary.

The top sheet 30 has a skin contact region 30E in contact with a skin of a wearer, and is preferably formed of a nonwoven fabric from a viewpoint of a liquid pervious property and texture. Various nonwoven fabrics can be used for the top sheet 30, but in consideration of a cushioning property, flexibility, a loose stool (watery feces or muddy feces) pervious property, and the like, a short fiber nonwoven fabric such as an air through nonwoven fabric is preferable rather than a long fiber (continuous fiber) nonwoven fabric, and a short fiber nonwoven fabric usually having a fineness of 1 to 10 dtex and a basis weight of 5 to 40 g/m², particularly having a basis weight of 10 to 30 g/m² and a thickness of about 0.4 to 1.4 mm is suitable. The fiber length of the short fiber nonwoven fabric is not particularly limited, but is preferably about 0.5 to 1.0 mm.

The top sheet 30 is particularly preferably a perforated nonwoven fabric having a hole arrangement region in which holes 14 penetrating the top sheet 30 from a front surface to a back surface are arranged substantially uniformly or in a predetermined pattern in order to enhance a loose stool pervious property. The shape, size, arrangement pattern, and the like of the holes 14 can be appropriately determined. Note that, in FIG. 1, the holes 14 are illustrated only in a part D of the top sheet 30 for the sake of visibility of the drawing, but this does not indicate the hole arrangement region.

The hole arrangement region can be only an intermediate region of the top sheet 30 in the front-back direction LD or only an intermediate region of the top sheet 30 in the width direction WD (a region having no hole 14 may be partially present). In addition, the hole arrangement region can be the entire top sheet 30. That is, as long as the hole arrangement region is disposed in the skin contact region, the hole arrangement region may spread to a region other than the skin contact region (for example, regions to which a gather sheet 62 is bonded on both sides in the width direction WD).

Figure 6:
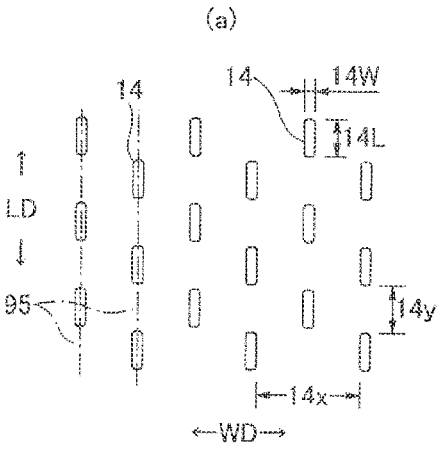
FIG. 6 is a plan view illustrating various examples of an arrangement pattern of holes of a perforated nonwoven fabric.
Figure 6:
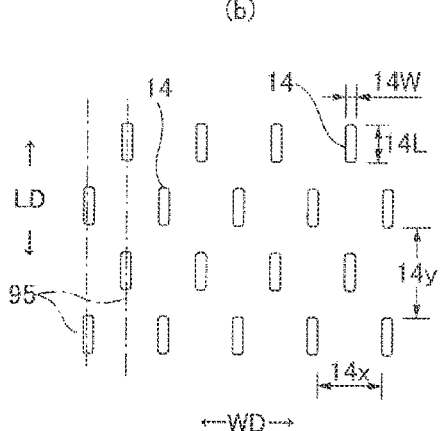
Figure 6:
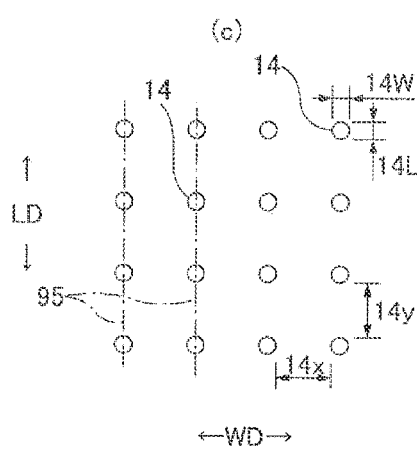
Figure 6:
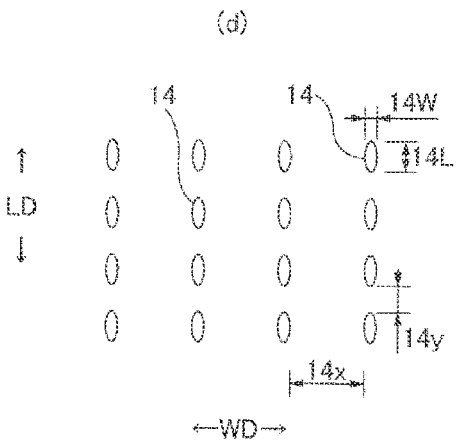
Figure 6:
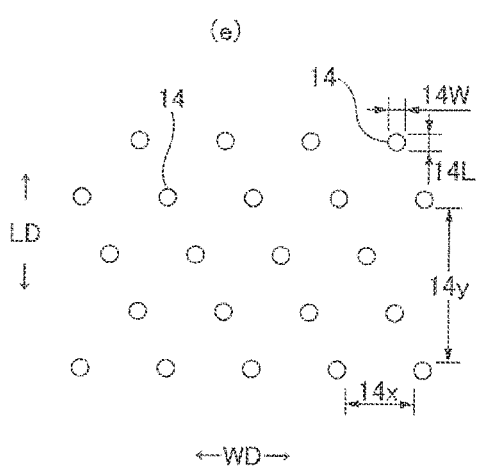
Figure 6:
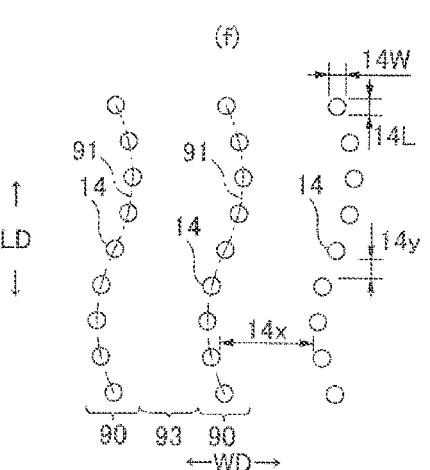

The planar shape (opening shape) of each of the holes 14 can be appropriately determined. In addition to the long hole shape as illustrated in FIGS. 6(a) and 6(b), the shape of the hole 14 can be an arbitrary shape such as a perfect circle as illustrated in FIGS. 6(c), 6(e), 6(f), 7, and 8, an ellipse as illustrated in FIG. 6(d), a polygon such as a triangle, a rectangle, or a rhombus, a star shape, or a cloud shape. Although not illustrated, holes 14 having different shapes may be mixed. The size of each of the holes 14 is not particularly limited. However, a size 14L in the front-back direction (size of the longest portion) is preferably 0.5 to 2.0 mm, and particularly preferably 0.5 to 2.0 mm. A size 14W in the width direction (size of the longest portion) is preferably 0.5 to 2.0 mm, and particularly preferably 0.5 to 1.0 mm. When the shape of the hole 14 is a shape elongated in the front-back direction (a shape in which a maximum length in one direction is longer than a maximum length in a direction orthogonal thereto) such as a long hole, an ellipse, a rectangle, or a rhombus, a size in the front-back direction is preferably 1.2 to 2.5 times a size in the width direction orthogonal thereto. When the shape of the hole 14 is a shape elongated in one direction, it is desirable that the longitudinal direction of the hole 14 is an MD (Machine Direction) direction of the nonwoven fabric, but may be a CD (Cross Direction) direction or an oblique direction inclined thereto. Note that the MD direction of the perforated nonwoven fabric forming the top sheet 30 is often equal to the front-back direction LD.

It is only required to appropriately determine the area of each of the holes 14 and an area ratio thereof in the hole arrangement region. However, the area is preferably about 0.25 to 4.00 mm², and the area ratio is preferably about 0.1 to 10%.

The arrangement pattern of the holes 14 can be appropriately determined. For example, as illustrated in FIGS. 6(a), 6(c), and 6(d), the arrangement pattern of the holes 14 is preferably a matrix in which a row of the holes 14 linearly arranged at predetermined intervals in the front-back direction LD is repeated at predetermined intervals in the width direction WD. In this case, as illustrated in FIGS. 6(a) and 6(d), an arrangement can be adopted in which an interval 14y between the holes 14 in the front-back direction LD is shorter than an interval 14x between the holes 14 in the width direction WD. In addition, as illustrated in FIG. 6(c), an arrangement can be adopted in which the interval 14y between the holes 14 in the front-back direction LD is almost equal to the interval 14x between the holes 14 in the width direction WD, or as illustrated in FIGS. 6(b) and 6(e), an arrangement can be adopted in which the interval 14y between the holes 14 in the front-back direction LD is longer than the interval 14x between the holes 14 in the width direction WD. As illustrated in FIGS. 6(b) and 6(e), an arrangement can be adopted in which hole rows 95 in each of which holes are linearly arranged at predetermined intervals in the front-back direction LD are arranged at intervals in the width direction WD so as to be shifted in the front-back direction LD. The examples illustrated in FIGS.

6(a) and 6(b) are each a so-called staggered (hexagonal lattice) arrangement in which the arrangement of the holes 14 is alternate in the adjacent hole rows 95.

The front-back direction interval 14y between the holes 14 and the width direction interval 14x between the holes 14 may be constant or may change. These can be determined appropriately. However, the front-back direction interval 14y between the holes 14 can be 0.9 to 8.0 mm, particularly 1.0 to 3.0 mm, and the width direction interval 14x between the holes can be 2.0 to 10 mm, particularly 3.0 to 5.0 mm.

Figure 7:
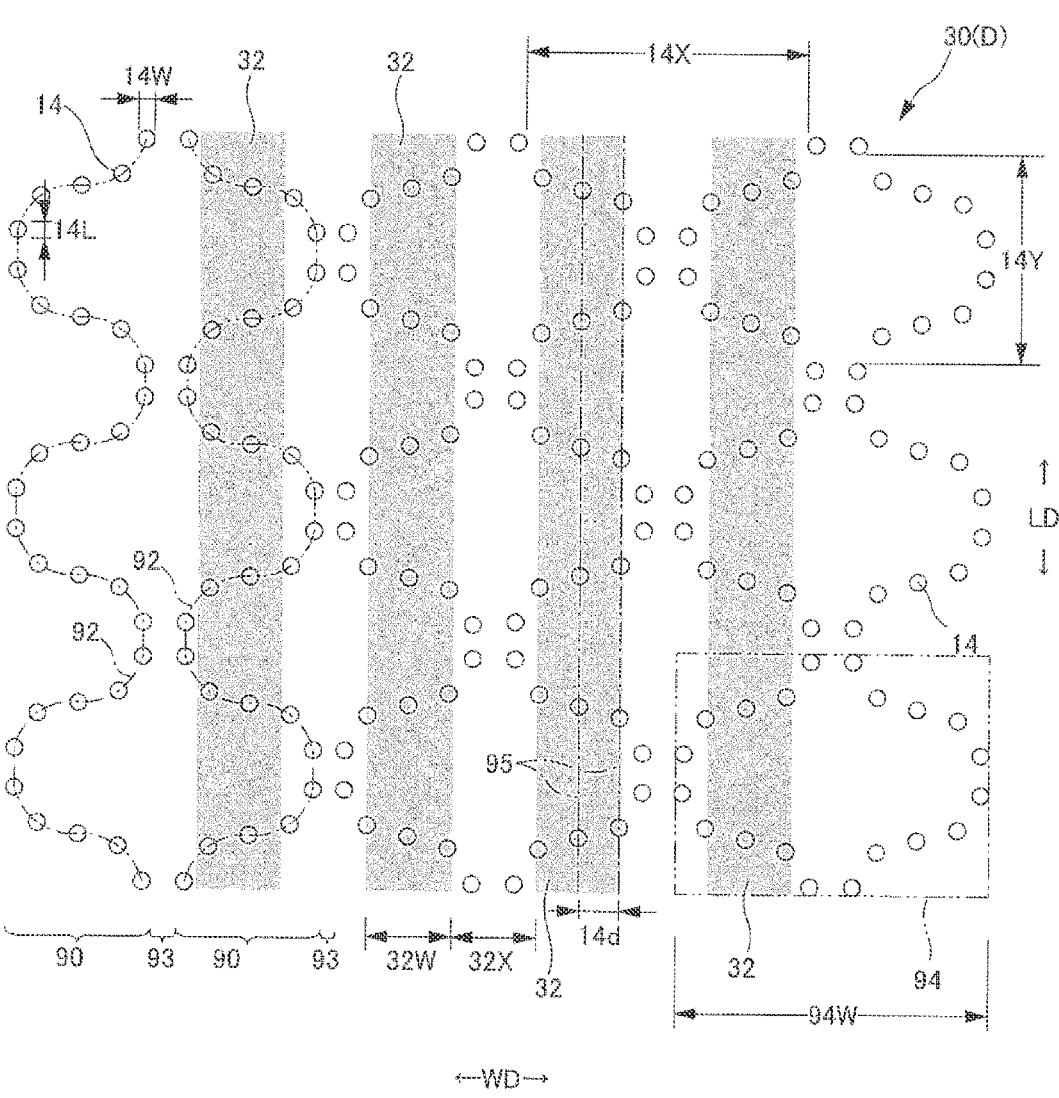
FIG. 7 is a plan view illustrating an example (moroccan pattern) of an arrangement pattern of holes of a perforated nonwoven fabric.
Figure 8:
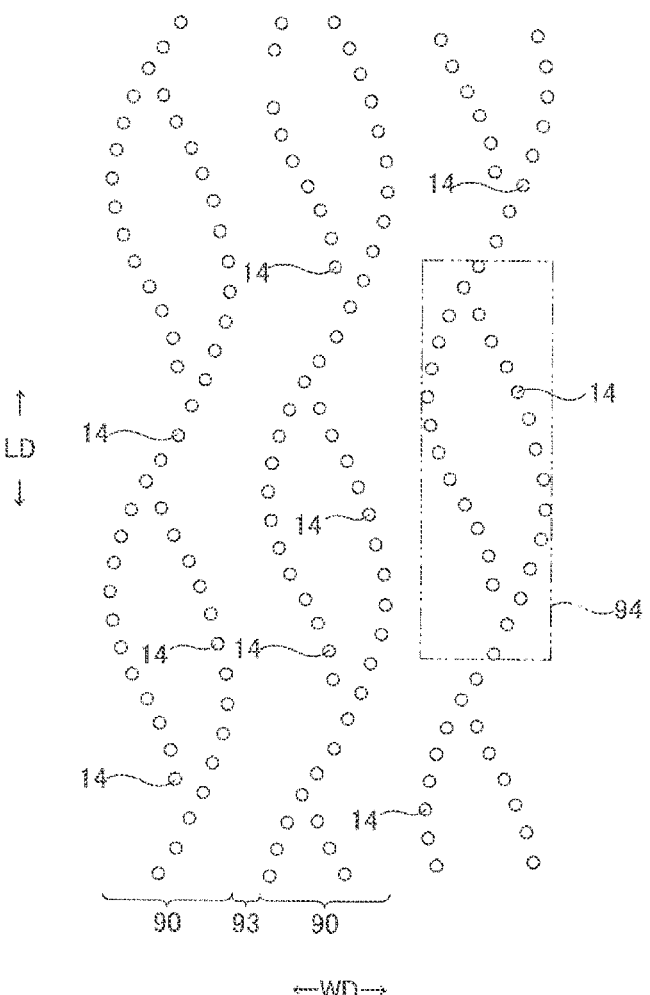
FIG. 8 is a plan view illustrating an example (chain pattern) of an arrangement pattern of holes of a perforated nonwoven fabric.

In addition, as illustrated in FIGS. 6(f) and 7, the arrangement pattern of the holes 14 can be a pattern in which groups 90 in each of which the holes 14 are arranged in a single wavy shape 91 or 92 continuous in the front-back direction LD are arranged in the same phase or different phases at intervals in the width direction WD. In the pattern of the example illustrated in FIG. 7, wavy phases of the groups 90 of the holes 14 adjacent in the width direction WD are opposite to each other, and an imaginary line connecting the holes 14 is a moroccan pattern. In addition, as illustrated in FIG. 8, the arrangement pattern of the holes 14 can be a pattern in which groups 90 in each of which the holes 14 are arranged at intervals in a chain shape continuous in the front-back direction LD are arranged at intervals in the width direction WD. Here, "the groups 90 of the holes 14 are arranged at intervals in the width direction WD" means that an imperforate portion 93 linearly continuous in the front-back direction LD is present between the groups 90 of the holes 14 adjacent to each other in the width direction WD.

Figure 9:
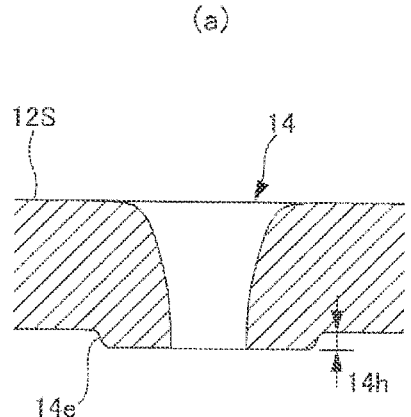
FIG. 9 is a cross-sectional view of a hole portion of a perforated nonwoven fabric.
Figure 9:
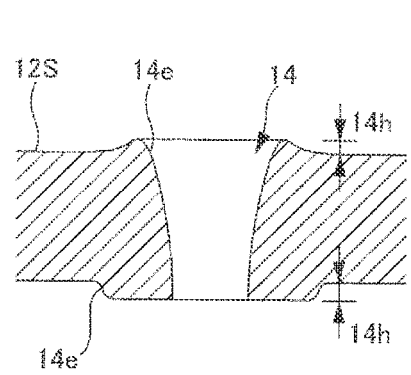
Figure 9:
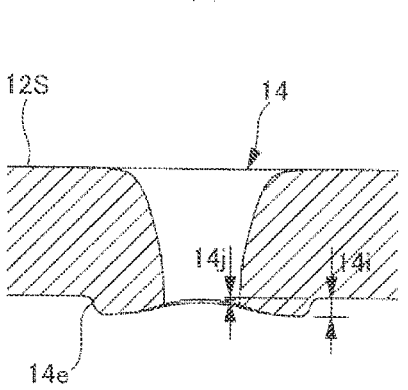
Figure 9:
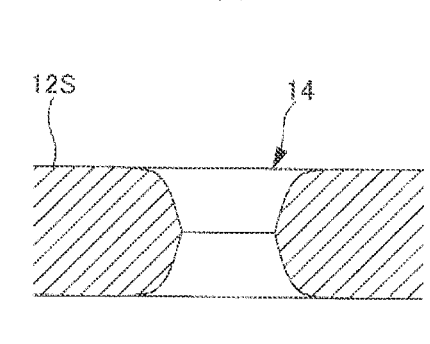

The cross-sectional shape of the hole 14 is not particularly limited. For example, the hole 14 may be a punched hole in which a peripheral edge is formed by a cut end of fibers, or may be a non-punched hole (having a high fiber density at an edge) in which there is almost no cut end of fibers at a peripheral edge of the hole 14 and a pin is inserted between fibers and expanded. As illustrated in FIG. 9(d), the punched hole may be a hole in which the diameter of the hole 14 decreases toward the middle in the thickness direction, or may be a hole in which the diameter of the hole 14 decreases toward one side in the thickness direction although not illustrated.

In the non-punched hole 14, the diameter of the hole 14 decreases from a pin insertion side toward the opposite side. This includes a hole in which the diameter of the hole 14 does not substantially decrease in the middle in the thickness direction in addition to a hole in which the diameter of the hole 14 continuously decreases over the entire nonwoven fabric layer in the thickness direction. Such a non-punched hole includes a hole in which a protruding portion (burr) 14e is formed at an edge of the hole 14 on the opposite side of a pin insertion side by extruding fibers to the opposite side of the pin insertion side, and the protruding portion 14e is not formed on the pin insertion side, as illustrated in FIGS. 9(a) and 9(c). Further, the non-punched hole includes a hole in which the protruding portion 14e is formed at an edge of the hole 14 on the opposite side of the pin insertion side by extruding fibers to the opposite side of the pin insertion side to the pin insertion side, and the protruding portion 14e is formed on the pin insertion side by extruding fibers to the pin insertion side, as illustrated in FIG. 9(b). Furthermore, the former type of hole 14 includes a hole in which a protruding height 14h of the protruding portion 14e is substantially uniform as illustrated in FIG. 9(a) and a hole in which the protruding portion 14e has a facing portion having a highest protruding height 14i and a facing portion facing in a direction orthogonal to the facing portion and having a lowest protruding height 14j as illustrated in FIG.

9(c). It is desirable that the protruding portion 14e is continuous in a circumferential direction of the hole to form a cylindrical shape, but the protruding portions 14e of some or all of the holes 14 may be each formed only in a part of the circumferential direction of the hole 14. The protruding heights 14h, 14i, and 14j (apparent heights in a state where pressure is not applied, which is measured using an optical microscope) are preferably about 0.2 to 1.2 mm. The highest protruding height 14i of the protruding portion 14e is preferably about 1.1 to 1.4 times the lowest protruding height 14j. The protruding height of the protruding portion 14e may change in the circumferential direction of the hole 14.

For example, when the hole 14 having a shape elongated in one direction as illustrated in FIGS. 6(a), 6(b), 6(d), and the like is formed by insertion of a pin, fibers at an edge of the hole 14 are retracted outward or in the vertical direction, and the protruding portion (burr) 14e in which the protruding height 14i of the facing portion of the hole 14 in the longitudinal direction is higher than the protruding height 14j of a facing portion in a direction orthogonal to the longitudinal direction is formed. The protruding portion 14e of the hole 14 may have a fiber density lower than a surrounding portion, but preferably has a fiber density almost equal to or higher than that of the surrounding portion.

In particular, in a case where the perforated nonwoven fabric is a long fiber nonwoven fabric having a fineness of 0.1 to 5.0 dtex (more preferably 1.0 to 3.0 dtex), a basis weight of 15 to 20 g/m² (more preferably 15 to 18 g/m²), and a thickness of 0.3 to 0.8 mm (more preferably 0.3 to 0.6 mm), when the hole 14 is formed by insertion of a pin, the protruding portion 14e formed at an edge of the hole 14 is lowered. More specifically, in the case of the long fiber nonwoven fabric in the above specific range, the fiber is hardly extruded in the thickness direction when the pin insertion hole is formed. This is because the fibers to which force is applied by the insertion of the pin are continuous (continuous fibers) while being entangled over the entire nonwoven fabric, and movement of the fibers in the portion to which force is applied by the insertion of the pin is suppressed by a portion connected to the outside thereof. Furthermore, since the long fiber nonwoven fabric in the above-described specific range basically has a moderately low fiber density, movement of the fibers in a direction orthogonal to the thickness direction is relatively easy. As a result, when the pin is inserted into the long fiber nonwoven fabric in the above-described specific range to form the hole 14 having the size in the above-described specific range, the fibers in the vicinity of the pin move toward a pin outlet side while being pushed out in a radial direction centered on a pin insertion direction at the time of insertion of the pin. Therefore, the height of the protruding portion 14e decreases although the protruding portion 14e is formed. Therefore, a high density portion having a higher fiber density than a surrounding portion is formed at the edge of the hole 14. There is an advantage that this high density portion makes shading between a surrounding portion of the hole and the hole stronger to improve visibility of the hole.

(Intermediate Sheet)

In order to rapidly transfer a liquid that has passed through the top sheet 30 to the absorber, it is possible to dispose the intermediate sheet (also referred to as "second sheet") 40 having a higher liquid permeation speed than the top sheet 30. The intermediate sheet 40 is used in order to rapidly transfer a liquid to the absorber to enhance absorption performance of the absorber, and to prevent a "returning" phenomenon of the absorbed liquid from the absorber. The intermediate sheet 40 can be omitted.

As the intermediate sheet 40, a liquid pervious sheet such as a nonwoven fabric can be used. In particular, an air through nonwoven fabric is preferable as the intermediate sheet 40 because of being bulky. As the air through nonwoven fabric, a composite fiber having a core-sheath structure is preferably used. In this case, a resin used for the core may be polypropylene (PP) but is preferably polyester (PET) having high rigidity. The basis weight is preferably 17 to 80 g/m², and more preferably 18 to 60 g/m². A raw material fiber of the nonwoven fabric preferably has a fineness of 2.0 to 10 dtex. In order to make the nonwoven fabric bulky, as mixed fibers of all or a part of raw material fibers, eccentric fibers having no core in the center, hollow fibers, eccentric and hollow fibers are also preferably used.

The intermediate sheet 40 in the illustrated example is disposed at the center so as to be shorter than the width of the absorber 56, but may be disposed over the maximum width. In addition, the intermediate sheet 40 may be disposed over the maximum length of the diaper, but may be disposed only in an intermediate portion in the front-back direction LD including an excrement position as in the illustrated example.

(Liquid Impervious Sheet)

The liquid impervious sheet 11 is not particularly limited, but preferably has moisture permeability. As the liquid impervious sheet 11, for example, a microporous sheet obtained by kneading an inorganic filler in a polyolefin-based resin such as polyethylene or polypropylene, molding a sheet, and then stretching the sheet in a monoaxial or biaxial direction can be suitably used. In addition, as the liquid impervious sheet 11, a sheet having improved water-proofness using a nonwoven fabric as a base material can also be used.

It is desirable that the liquid impervious sheet 11 extends within the same range as or a wider range than the absorber 56 in the front-back direction LD and the width direction WD. However, for example, when another water blocking means is present, an end portion of the absorber 56 does not have to be covered in the front-back direction LD and the width direction WD as necessary.

(Exterior Nonwoven Fabric)

The exterior nonwoven fabric 12 covers the entire back surface side of the liquid impervious sheet 11 and imparts a cloth-like appearance to a product outer surface. The exterior nonwoven fabric 12 has a fiber basis weight of preferably 10 to 50 g/m², particularly preferably 15 to 30 g/m², but the basis weight is not limited thereto. The exterior nonwoven fabric 12 can be omitted, and in this case, the liquid impervious sheet 11 can be extended to a side edge of the product.

(Rising Gather)

In order to block excrement that moves laterally on the top sheet 30 and to prevent so-called side leakage, rising gathers 60 rising on a skin side of a wearer are preferably disposed on both sides of a surface in the width direction WD. Of course, the rising gathers 60 can be omitted.

When the rising gather 60 is adopted, a structure thereof is not particularly limited, and any known structure can be adopted. The rising gather 60 in the illustrated example includes a gather sheet 62 substantially continuous in the width direction WD, and an elongated gather elastic member 63 fixed to the gather sheet 62 in a stretched state in the front-back direction LD. A water repellent nonwoven fabric can be used as the gather sheet 62, and a rubber thread or the like can be used as the gather elastic member 63. As

Figure 2:
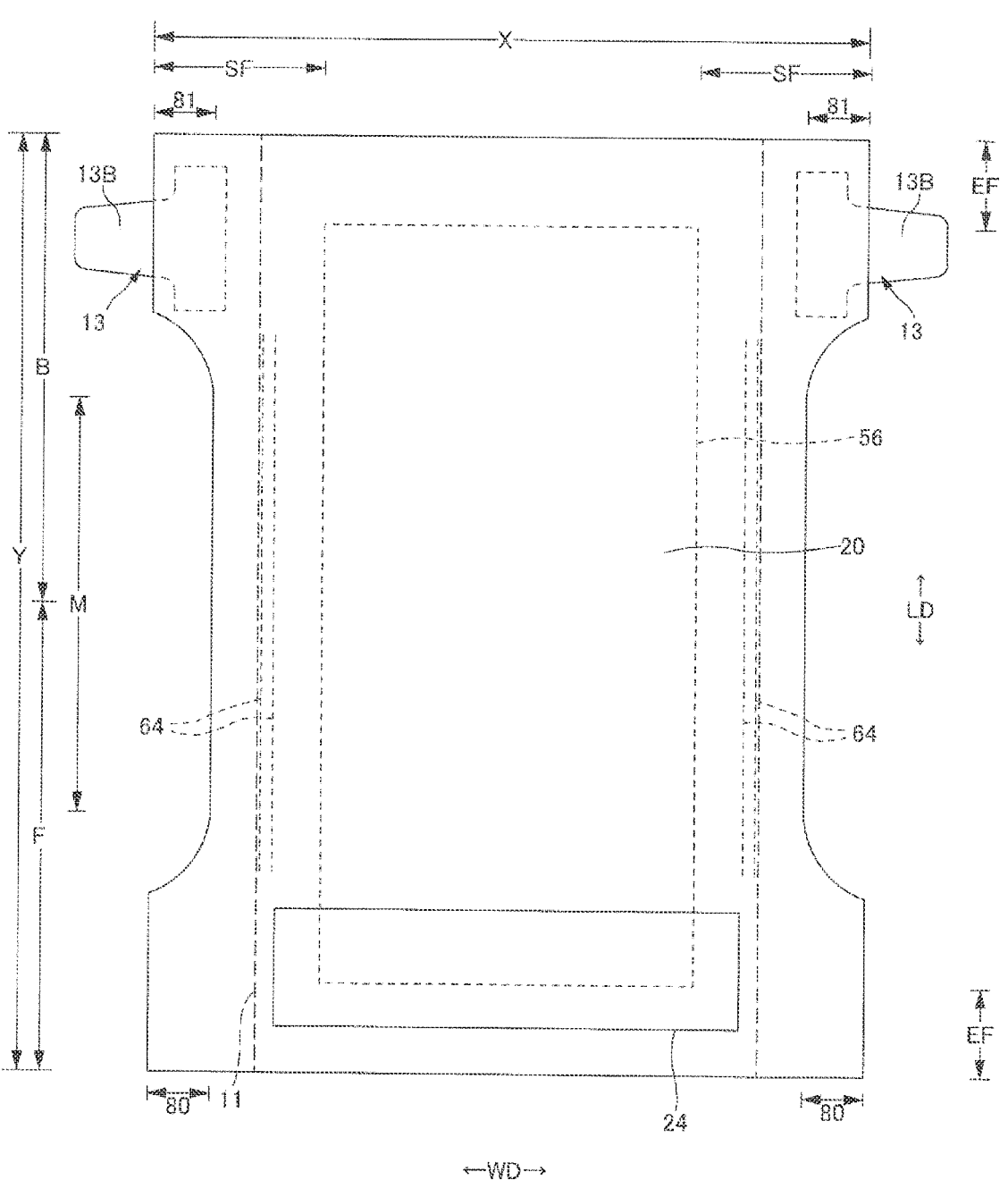
FIG. 2 is a plan view illustrating an outer surface of the tape-type disposable diaper in an unfolded state.

10 illustrated in FIGS. 1 and 2, a plurality of elastic members may be disposed, or one elastic member may be disposed.

An internal surface of the gather sheet 62 has a bonding start edge in the width direction WD on a side portion of the top sheet 30. A portion from the bonding start edge to the outside in the width direction is bonded to an internal surface of each side flap SF, that is, in the illustrated example, bonded to a side portion of the liquid impervious sheet 11 and a side portion of the exterior nonwoven fabric 12 located in an outside thereof in the width direction with a hot melt adhesive or the like.

In a periphery of a leg, a side closer to the center in the width direction than the bonding start edge of the rising gather 60 is fixed to the top sheet 30 at both end portions in a product front-back direction. However, a portion therebetween is a non-fixed free portion, and the free portion rises by a contraction force of the elastic member 63 and comes into close contact with a body surface.

(End Flap and Side Flap)

The tape-type disposable diaper in the illustrated example has a pair of end flaps EF not including the absorber 56 and extending to a front side and a back side of the absorber 56, and a pair of side flaps SF not including the absorber 56 and extending to lateral sides more than both side edges of the absorber 56. As in the illustrated example, the side flap SF may be formed of a main body sheet (exterior nonwoven fabric 12 or the like) continuous from a portion having the absorber 56, or may be formed by attaching another material.

(Plane Gather)

To each side flap SF, a side elastic member (leg periphery elastic member) 64 formed of an elongated elastic member such as a rubber thread is fixed in a stretched state in the front-back direction LD, and a periphery of a leg of each side flap SF is thereby configured as a plane gather. The leg periphery elastic member 64 can be disposed between the gather sheet 62 and the liquid impervious sheet 11 outside the vicinity of the bonding start edge in the width direction in the bonded portion of the gather sheet 62 as in the illustrated example, and can also be disposed between the liquid impervious sheet 11 and the exterior nonwoven fabric 12 in the side flap SF. A plurality of the leg periphery elastic members 64 may be disposed on each side as in the illustrated example, or only one leg periphery elastic member 64 may be disposed on each side. Of course, the leg periphery elastic member 64 (plane gather) can be omitted.

The plane gather is a portion where a contraction force of the side elastic member 64 acts (a portion where the side elastic member 64 is illustrated in the drawing). Therefore, in addition to a form in which the side elastic member 64 is present only in the site of the plane gather, a structure is also included in which the side elastic member 64 is present on the front side, the back side, or both sides of the plane gather, but the side elastic member is finely cut at one or many portions other than the site of the plane gather and/or is not fixed to sheets sandwiching the side elastic member 64 therebetween, and the contraction force of the side elastic member 64 thereby acts only on the site of the plane gather without acting on a site other than the plane gather (substantially equivalent to no elastic member).

(Front Wing)

The present tape-type disposable diaper has the front wings 80 protruding to both left and right sides at positions away in the front side of the center of the product in the front-back direction. The front wings can be omitted (that is, a shape can be adopted in which the width does not change from a portion of the product having the narrowest width to the front end of the product).

The size of the front wing 80 in the width direction WD can be appropriately determined, and can be, for example, 5 to 20% (particularly 7 to 15%) of the maximum length Y of the article. The size of the front wing 80 in the width direction WD can be substantially the same as the size of the back wing 81 in the width direction WD described later.

(Back Wing)

The present tape-type disposable diaper has the back wings 81 protruding to both left and right sides at positions away in the back side of the center of the product in the front-back direction.

The size of the back wing 81 in the width direction WD can be appropriately determined, and can be the same as the size of the front wing 80 in the width direction, or can be smaller or larger than the size of the front wing 80 in the width direction.

(Intermediate Portion)

Both side edges 15 of the product between the front wings 80 and the back wings 81 can each have, for example, a substantially linear portion passing through a range of widths of ±5 mm in a direction orthogonal to a center which is a direction in which a smaller angle formed by intersecting with respect to the front-back direction LD is less than ±2 degrees. The both side edges 15 of the product between the front wings 80 and the back wings 81 may be wavy or arcuate (not illustrated) or linear as in the illustrated example.

(Formation of Wing)

As in the illustrated example, by cutting the side portion of the side flap SF in a recessed shape, an entire recessed edge from a lower edge of the front wing 80 through each of the side edges 15 of the product between the front wing 80 and the back wing 81 to a lower edge of the back wing 81 can be formed. In this case, a stacked structure of the front wing 80 and the back wing 81 is determined by a stacked structure of the side flap SF, and in the illustrated example, the front wing 80 and the back wing 81 are formed by the gather sheet 62 and the exterior nonwoven fabric 12. Although not illustrated, a front extension sheet protruding to a lateral side from the side flap SF may be disposed, and the entire front wing 80 or a part of a distal end side may be formed by the front extension sheet. Similarly, a back extension sheet protruding to a lateral side from the side flap SF may be disposed, and the entire back wing 81 or a part of a distal end side may be formed by the back extension sheet. As the front extension sheet and the back extension sheet, various nonwoven fabrics can be used.

(Connecting Portion)

The back wing 81 includes a connecting portion 13A to be detachably connected to the ventral side portion F when the diaper is worn. That is, when the diaper is worn, both side portions of the back wings 81 are carried to a ventral side of a wearer, and the connecting portions 13A of the back wings 81 are connected to an outer surface of the ventral side portion F. As the connecting portion 13A, a hook material (male member) of a mechanical fastener (hook and loop fastener) or an adhesive layer may be disposed. The hook material has many engaging projections on a connecting surface thereof. As the shape of the engaging projection, any known shape such as a tick shape, a J shape, a mushroom shape, a T shape, or a double J shape (a shape in which J-shaped ones are connected to each other back to back) can be adopted.

The connecting portion 13A can be directly attached to the back wing 81, or as in the illustrated example, a connecting tape 13 having the connecting portion 13A can be attached to the back wing 81. The structure of the connecting tape 13 is not particularly limited. However, in the illustrated example, the connecting tape 13 includes: a tape attachment portion 13C fixed to the side flap SF; a tape main unit portion 13B protruding from the tape attachment portion 13C; and the connecting portion 13A disposed at an intermediate portion of the tape main unit portion 13B in the width direction WD, and a distal end side of the connecting portion 13A is a tab part. As a sheet material forming a portion from the tape attachment portion 13C to the tape main unit portion 13B, a nonwoven fabric, a plastic film, a polylaminated nonwoven fabric, paper, or a composite material thereof can be used.

A connection point of the connecting portion 13A on an outer surface of the ventral side portion F can be appropriately determined, and only the main unit portion located between the left and right front wings 80 may be used as the connection point, or a range from a side portion of the main unit portion to a base edge side of the front wing 80 may be used as the connection point. At these connecting portions, connecting of the connecting portion 13A is preferably easy. For example, in a case where the connecting portion 13A is a hook material (male member) of a mechanical fastener (hook and loop fastener), the connecting portion on the outer surface of the ventral side portion F only needs to be formed of a loop material (female member) of a mechanical fastener or a nonwoven fabric. As the loop material, one in which a loop thread is sewn to a plastic film is also known, but one in which a welded portion in which fibers are intermittently welded to each other at least in the width direction WD is disposed on a long fiber nonwoven fabric (for example, a spunbonded nonwoven fabric having a fineness of 2.0 to 4.0 dtex, a basis weight of 20 to 50 g/m$^2$, and a thickness of about 0.3 to 0.5 mm) in which a fiber continuous direction is the width direction WD is preferable from a viewpoint of air permeability and flexibility. In a case where a region including the connecting portion on the outer surface of the ventral side portion F is formed of the exterior nonwoven fabric 12 as in the illustrated example, a hook material can be connected to the exterior nonwoven fabric 12 without adding anything. If necessary, the loop material may be attached only to the connection portion on the outer surface of the ventral side portion F. In a case where the connecting portion 13A is a pressure sensitive adhesive material layer, a plastic film having a smooth surface with high pressure sensitive adhesion can be attached to the connecting portion on the outer surface of the ventral side portion F.

(Fixation of Top Sheet)

The top sheet 30 is preferably bonded to a member on a back surface side disposed on a back surface side of the top sheet 30 via a hydrophobic hot melt adhesive 31. Alternatively or in addition, the top sheet 30 may be bonded to the member on the back surface side disposed on the back surface side thereof by welding of at least one of the top sheet 30 and the member on the back surface side disposed on the back surface side thereof. A top sheet 30 fixing region may extend to a region other than the hole arrangement region (for example, the entire top sheet 30) or may be only the hole arrangement region as long as the top sheet 30 fixing region extends at least over the entire hole arrangement region. In the illustrated example, the members on the back surface side are the intermediate sheet 40, the wrapping sheet 58, and the liquid impervious sheet 11, but are not limited thereto.

As the hydrophobic hot melt adhesive 31, an EVA-based agent, a polyolefin-based agent, a polyester/polyamide-based agent, and the like can be used, and in particular, a pressure sensitive adhesive rubber-based agent (elastomer-based agent) can be suitably used.

An application amount of the hydrophobic hot melt adhesive 31 can be appropriately determined, but can be usually about 0.1 to 10 g/m$^2$. In particular, when the application amount of the hydrophobic hot melt adhesive 31 is about 0.5 to 5 g/m$^2$, protrusion of the hot melt adhesive 31 from the hole 14 can be suppressed, which is preferable, but adhesion inhibition by glycerin, which will be described later, is likely to occur, and thus, it is desirable to combine the application amount with contrivance of a glycerin coating pattern or the like. The coating pattern of the hydrophobic hot melt adhesive 31 can be appropriately determined, and a dense pattern in which minute non-applied portions are scattered (spray application in a spiral shape, a Z shape, a wavy shape, or the like) is suitable, but a coating pattern applied in solid coating, such as slot application may be used.

(Prevention of Rash)

A skin contact region of the top sheet 30 which may be contact with a skin of a wearer (region in a state where the rising gather 60 has risen), specifically, in the embodiment, a skin contact region 30E between side edges of the rising gather 60 (region exposed to a surface of the article in an unfolded state) are regions where rash may occur when the disposable wearing article is worn.

A treatment agent containing a nonionic surfactant (A) described later is applied in advance to the entire top sheet 30, preferably the entire skin contact region 30E, or at least a glycerin-containing region 32 to which glycerin is applied and in which glycerin is contained in the top sheet 30.

(Glycerin-Containing Region)

Figure 10:
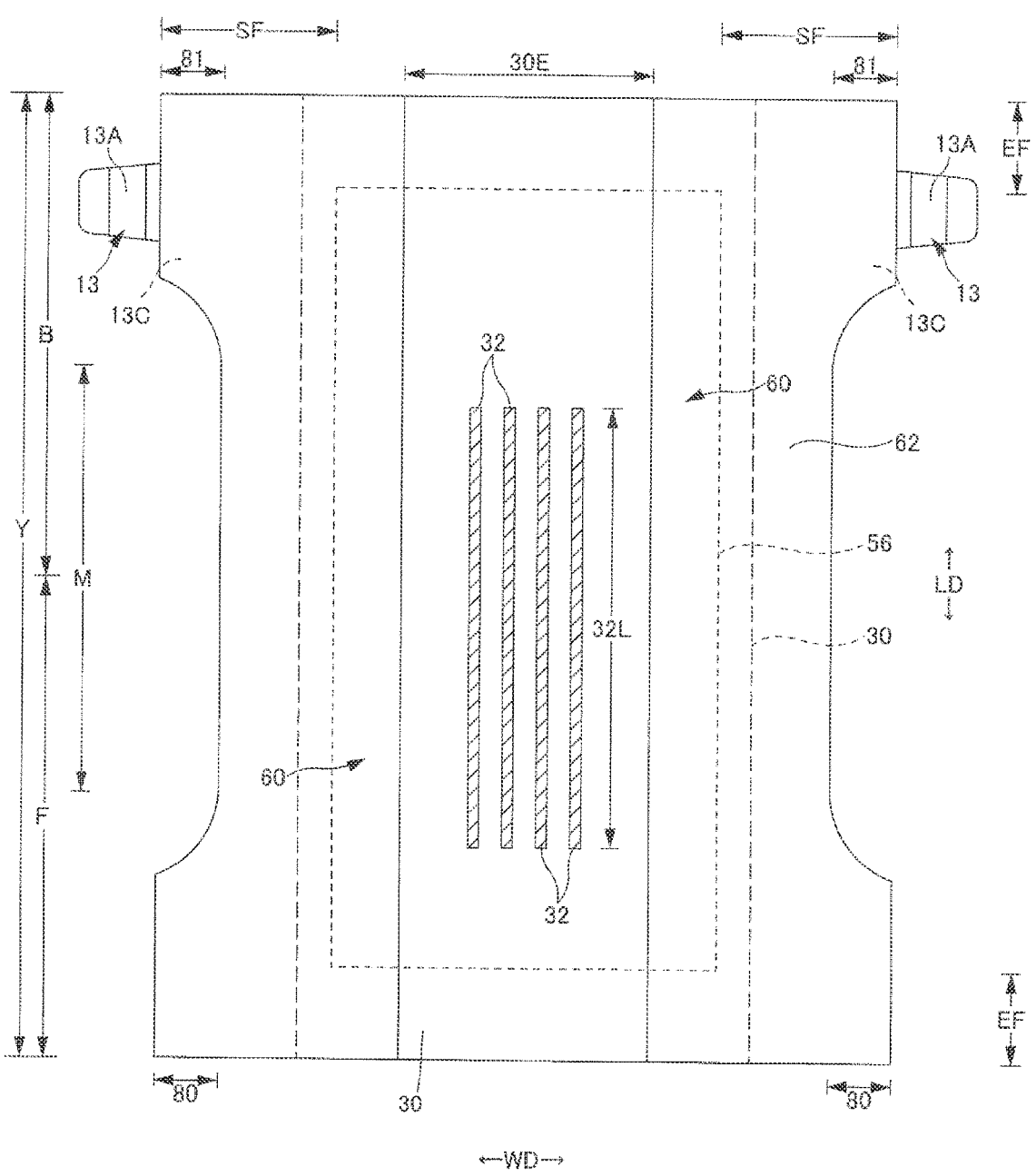
FIG. 10 is a plan view illustrating an inner surface of a tape-type disposable diaper in an unfolded state.
Figure 11:
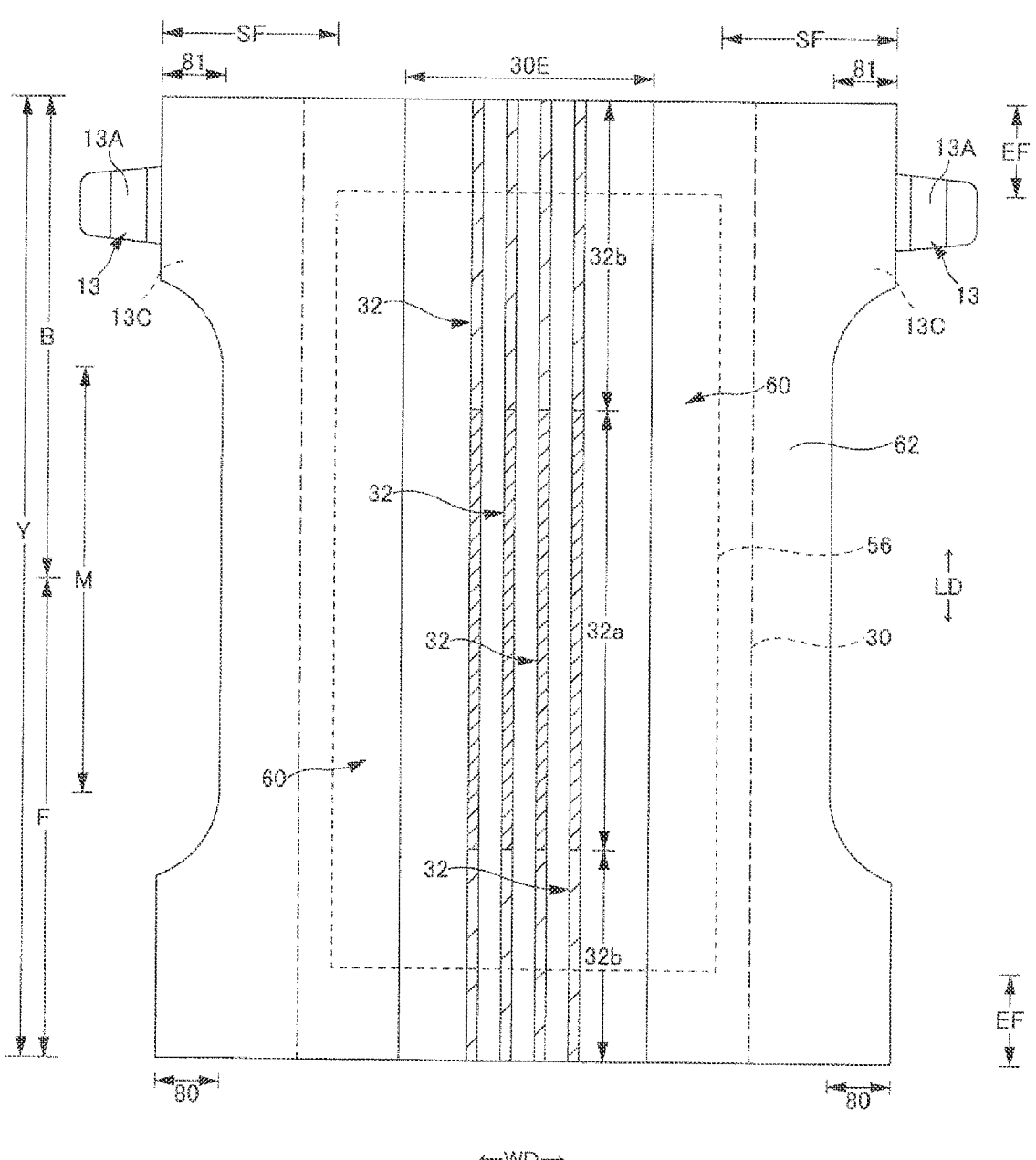
FIG. 11 is a plan view illustrating an inner surface of a tape-type disposable diaper in an unfolded state.

As illustrated in FIGS. 7, 10, and 11, the skin contact region 30E of the top sheet 30 has the glycerin-containing region 32 containing 0.7 to 2.7 g/m$^2$ of glycerin. The glycerin-containing region 32 may be disposed at only one place with a certain large area or at a plurality of places. The glycerin-containing region 32 may be disposed or does not have to be disposed in a region other than the skin contact region 30E of the top sheet 30 as long as the glycerin-containing region 32 is disposed in the skin contact region 30E.

The size, arrangement, and the like of the glycerin-containing region 32 can be appropriately determined. Note that it is not preferable that the size of the glycerin-containing region is too small because it is difficult to obtain a rash preventing effect, and it is preferable that one glycerin-containing region 32 has a size 32L in the MD direction (front-back direction LD in the illustrated example) of 5 mm or more and a size 32W in the CD direction (width direction WD in the illustrated example) of 5 mm or more. The size 32L of the glycerin-containing region 32 in the MD direction is more preferably 30 mm or more, still more preferably 50 mm or more, and particularly preferably 100 mm or more. An upper limit of the size 32L of the glycerin-containing region 32 in the MD direction is the product maximum length Y, but may be shorter than this. The size 32W of the glycerin-containing region 32 in the CD direction is more preferably 10 mm or more. An upper limit of the size 32W of the glycerin-containing region 32 in the CD direction is the size of the top sheet 30 in the width direction WD, but may be shorter than this.

In addition, when the area of the glycerin-containing region 32 in the skin contact region 30E is too small, a moisturizing agent attaching effect to a skin and a friction reducing effect are poor. Therefore, an area ratio of the glycerin-containing region 32 in the skin contact region 30E (total area of glycerin-containing region 32/area of skin contact region 30E x 100) is preferably 3% or more, and particularly preferably 5% or more. Note that the skin contact region 30E means a region exposed to a surface of the article in an unfolded state as described above. Therefore, when a part of the top sheet 30 is hidden by another member in an unfolded state (both side portions of the top sheet 30 are hidden by the rising gather 60 in the illustrated example), the skin contact region 30E means a region excluding the hidden portion. When the entire surface of the top sheet 30 is exposed to the surface of the product, the skin contact region 30E means the entire surface itself.

As in the illustrated example, the glycerin-containing region 32 is preferably disposed in a longitudinal stripe shape in which glycerin is applied in a manufacturing line direction. A lateral stripe shape, a dotted pattern shape, or a lattice pattern shape may be used. In these cases, an interval 32X between the adjacent glycerin-containing regions 32 can be appropriately determined, but is preferably, for example, about 1.5 to 10 mm.

As the nonwoven fabric of the top sheet 30, a nonwoven fabric having a fineness of 1 to 3 dtex (more preferably 1.5 to 2.5 dtx), a basis weight of 10 to 30 g/m$^2$ (more preferably 15 to 25 g/m$^2$), and a thickness of 0.4 to 1.4 mm (more preferably 0.5 to 1.0 mm) is preferably adopted.

That is, in such a nonwoven fabric, the fineness of fibers contributes to reduction of friction on a surface, and a friction reducing effect as a whole is improved together with a friction reducing effect by glycerin. In addition, retention of glycerin is also improved due to the fineness of fibers, and this also improves the friction reducing effect.

Furthermore, glycerin contained in the top sheet 30 is transferred to a skin of a wearer (particularly, permeates into a horny layer), and the skin of the wearer can be thereby moisturized (prevented from being dried). In short, a physical irritation reducing action on the skin of the wearer and a moisturizing action on the skin of the wearer are highly compatible, and in particular, an excellent rash preventing effect can be obtained. In particular, an average friction coefficient MIU of the glycerin-containing region 32 in the top sheet 30 is preferably 0.2 to 0.4 by a combination of the nonwoven fabric and glycerin. The nonwoven fabric of the top sheet 30 is particularly preferably a short fiber nonwoven fabric from these viewpoints.

A surface water ratio of the glycerin-containing region 32 is not particularly limited, but is preferably 3 to 10%, and particularly preferably 4 to 8% because a skin of a wearer can be moderately moistened to prevent the skin from being dried.

In order to form the glycerin-containing region 32, a hydrophilic lotion containing glycerin can be applied in a desired pattern to the top sheet 30 to which a body fluid pervious agent (body fluid pervious treatment agent) described in detail later is applied. A particularly preferred hydrophilic lotion contains 70 to 90% by weight of glycerin and 10 to 30% by weight of water. As described above, the hydrophilic lotion containing glycerin as a main component and an appropriate amount of water is not only preferable as a moisturizing agent when the hydrophilic lotion is transferred to a skin but also preferable because water is retained in glycerin as bonded water (glycerin has extremely high water retention), and thus the hydrophilic lotion is less likely to decay. That is, from such a viewpoint, in a case of using a hydrophilic lotion containing water, when the hydrophilic lotion contains a large amount of glycerin and a water activity value of the hydrophilic lotion is suppressed to a low value, for example, 0.8 or less, more preferably 0.3 to 0.7, particularly preferably 0.3 to 0.5 while a surface water ratio is sufficiently ensured (for example, 3 to 10% described above), propagation of microorganisms is suppressed even when the hydrophilic lotion contains no preservative, pre-servability is favorable, and a moisturizing effect when the hydrophilic lotion is transferred to a skin is also high.

The hydrophilic lotion can contain, as an additive, one or more additives selected from the group consisting of an emulsifier, a phosphate, a paraffin, and a surfactant. As the surfactant, an ether type nonionic surfactant and a nonionic surfactant containing an EO/PO type are preferable. In order to improve preservability of the product, the hydrophilic lotion may contain a preservative. However, since the hydro-philic lotion is transferred to a skin to moisturize the skin, it is desirable that the hydrophilic lotion contains no preser-vative.

The content of glycerin in the glycerin-containing region 32 is desirably 0.7 to 2.7 $g/m^2$, and more preferably 1.0 to 2.2 $g/m^2$. As an example, when the glycerin-containing region is formed by applying a hydrophilic lotion containing 70 to 90% by weight of glycerin and 10 to 30% by weight of water to the top sheet, the application amount of the hydrophilic lotion in the glycerin-containing region 32 can be about 5 to 15 $g/m^2$. As in the example illustrated in FIG. 11, in a case where there is a plurality of regions having different contents of the hydrophilic lotion, or in a case where the application amount of the hydrophilic lotion is continuously changed, the application amount of the hydro-philic lotion in the entire glycerin-containing region 32 may be less than or more than the above content range as long as there is a portion within the above content range.

Note that the content of glycerin is measured by the following glycerin content measurement method.

(Glycerin Content Measurement Method)

Four identical products are prepared, and for any one of them, the size of the glycerin-containing region 32 is measured by a method described later, and the area of the glycerin-containing region 32 (the total area when there is a plurality of glycerin-containing regions) is determined.

All the glycerin-containing regions 32 are cut out from the top sheets 30 for the four identical products (it is not necessary to accurately cut out the glycerin-containing region 32 along an edge, and as long as the entire glycerin-containing region is included, a portion sur-rounding the glycerin-containing region may be slightly included), and all the glycerin-containing regions 32 thus cut out are used as test pieces, or the top sheets 30 for the four identical products are removed and used as they are as test pieces.

The test pieces are put in a 300 ml beaker containing water at a temperature of 25° C., and irregular poking or stirring with a glass rod is repeated for one minute or more. Thereafter, the test pieces are allowed to stand in a state of being immersed in water for 60 minutes. While the test pieces are allowed to stand, the test pieces are folded and a weight is placed on the test pieces such that the heights of the test pieces in the beaker are as low as possible, or the test pieces are fixed in advance by adhesion or sewing in a state of being folded. In addition, the amount of water is set to a minimum amount (for example, 10 ml) at which the entire test pieces can be immersed in water. After the test pieces are allowed to stand, irregular poking or stirring with a glass rod is repeated for one minute or more. Thereafter, the test pieces are lifted up and sufficiently squeezed, and a glycerin concentration of the glycerin-containing water remaining in the beaker is measured with a glycerin concentration meter. In addition, the weight of the glycerin-containing water remaining in the beaker is measured. Then, the weight of glycerin contained in the glycerin-containing water is determined on the basis of these measurement results.

The weight of glycerin ($g/m^2$) of the glycerin-containing region 32 is calculated by dividing the glycerin weight of the glycerin-containing water by a value obtained by multiplying the area of the glycerin-containing region 32 by 4 (for four products).

As the nonwoven fabric of the top sheet 30, a nonwoven fabric using fibers of a hydrophobic resin is preferable because of low cost. However, the nonwoven fabric using fibers of a hydrophobic resin itself has poor retention of glycerin when a hydrophilic lotion containing water is used. Therefore, the hydrophilic lotion preferably has a viscosity of 150 to 400 mPa·s at a temperature of 20° C. In this way, it is preferable to enhance the retention of glycerin in the nonwoven fabric.

For a similar reason, it is preferable to use a nonwoven fabric of hydrophilic fibers in which a hydrophilizing agent is applied to fibers of a hydrophobic resin for the top sheet. In this way, it is preferable to enhance the retention of glycerin in the nonwoven fabric.

As the hydrophilizing agent, a nonionic activator obtained by adding ethylene oxide to a higher alcohol, a higher fatty acid, an alkyl phenol, or the like, an anionic activator such as an alkyl phosphate (octyl-based or dodecyl based) or an alkyl sulfate, or the like is preferably used alone or in mixture thereof in consideration of safety to a human body, safety in a process, and the like. The amount of the hydro-philizing agent to be applied varies depending on required performance, but it is desirable that the amount of the hydrophilizing agent to be applied is usually about 0.1 to 2.0% by weight, and particularly about 0.2 to 1.0% by weight with respect to the dry weight of a target sheet.

(Body Fluid Pervious Treatment Agent)

A major factor of rash in the disposable wearing article is that an excreted body fluid remains on the top sheet and comes into contact with a skin of a wearer. In particular, in a case where the excreted body fluid is loose stool, this is a major factor of rash.

In this case, it has been found that it is desirable to apply the nonionic surfactant (A) as a body fluid pervious treat-ment agent after manufacturing a nonwoven fabric to which hydrophilicity is imparted by, for example, treating fibers with the above-described hydrophilizing agent at a stage of manufacturing the nonwoven fabric constituting the top sheet.

In particular, it is effective to use the nonionic surfactant (A) having an amide and/or amino group, more suitably the nonionic surfactant (A) having an amide group, and it is desirable that a region to which the body fluid pervious treatment agent containing the nonionic surfactant (A) is applied includes the above-described glycerin-containing region to which glycerin is applied.

A reason why it is effective not to treat a nonwoven fabric with the nonionic surfactant (A) at a stage of manufacturing the nonwoven fabric but to apply the surfactant after the nonwoven fabric is manufactured, particularly to apply the surfactant in a line of manufacturing the disposable wearing article, more suitably to apply the surfactant by spraying or the like from a use surface side toward a back surface side of the top sheet, is considered to be that the surfactant attaches to a space between fibers of the top sheet to activate an interface around a space through which a body fluid, particularly loose stool passes.

If necessary, the nonwoven fabric can be treated with the nonionic surfactant (A) in advance at a stage of manufacturing the nonwoven fabric. However, it cannot be substantially recognized that a body fluid pervious effect is enhanced, and the number of treatment steps only increases. Therefore, the treatment with the nonionic surfactant (A) in advance at a stage of manufacturing the nonwoven fabric is unnecessary.

Then, the treatment agent containing the nonionic surfactant (A) is applied to the nonwoven fabric, and glycerin is applied to a region where hydrophilicity is particularly enhanced, whereby glycerin favorably remains in the vicinity of a surface of the nonwoven fabric, and exhibits a moisturizing effect for a long time.

As the nonionic surfactant (A), an alkanol nonionic surfactant (A) having an amide group is particularly desirable.

It is more desirable to use the nonionic surfactant (A) alone, not in combination with another surfactant such as an anionic surfactant, a cationic surfactant, or an amphoteric ion-based surfactant.

In a preferred embodiment, the nonionic surfactant (A) is applied after the nonwoven fabric is manufactured, in particular, the nonionic surfactant (A) is applied in a line of manufacturing the disposable wearing article. Therefore, for example, as illustrated in Patent Literature 2 described above, it is not necessary to impart "antistatic properties" with an amphoteric surfactant in consideration of a stage of manufacturing the nonwoven fabric by a carding method (a method for manufacturing a web through a roller carding machine), and an amphoteric surfactant is unnecessary.

Furthermore, use of a single nonionic surfactant (A) is more desirable than use of nonionic surfactants (A) having different HLB values in combination.

Examples of the nonionic surfactant (A) include an aliphatic alcohol (8 to 24 carbon atoms) alkylene oxide (2 to 8 carbon atoms) adduct (polymerization degree=1 to 100) oxyalkylene (2 to 8 carbon atoms, polymerization degree: 1 to 100) higher fatty acid (8 to 24 carbon atoms) ester, a polyvalent (divalent to 10 valent or higher) alcohol fatty acid (8 to 24 carbon atoms) ester, a (poly)oxyalkylene (2 to 8 carbon atoms, polymerization degree: 1 to 100) polyvalent (divalent to 10 valent or higher) alcohol higher fatty acid (8 to 24 carbon atoms) ester, a fatty acid alkanolamide, a (poly)oxyalkylene (2 to 8 carbon atoms, polymerization degree: 1 to 100) alkyl (1 to 22 carbon atoms) phenyl ether, a (poly)oxyalkylene (2 to 8 carbon atoms, polymerization degree: 1 to 100) alkyl (8 to 24 carbon atoms) aminoether, and an alkyl (8 to 24 carbon atoms) dialkyl (1 to 6 carbon atoms) amine oxide.

In particular, the fatty acid alkanolamide is suitable from viewpoints that the fatty acid alkanolamide exhibits an appropriate HLB value and the amide group enhances a body fluid pervious property.

Meanwhile, the HLB value of the nonionic surfactant (A) is suitably 7 to 17 and preferably 8 to 15 when it is considered that lipophilicity is also required to some extent from a viewpoint of a pervious property of a body fluid containing oils, such as loose stool.

The HLB value in the present invention is an HLB value according to the Oda method, which is a hydrophilic-hydrophobic balance value, and can be calculated from a ratio between an organic value and an inorganic value of an organic compound.

$$HLB \approx 10 \times inorganic/organic$$

In addition, the inorganic value and the organic value are described in detail on page 501 of the document "Synthesis of Surfactant and Applications thereof" (Published by Maki Shoten, written by Oda and Teramura).

As a method for applying the treatment agent to the top sheet, an appropriate form such as non-contact type summit, spiral, signature, one-fluid or two-fluid spray, a contact type slot coater, or a printing type hammer roll can be adopted, but a one-fluid or two-fluid spray is desirable in terms of permeability into a space between nonwoven fabric fibers.

The attachment amount of the body fluid pervious treatment agent (loose stool pervious treatment agent) to the fibers is preferably 0.05 to 2% by weight, and more preferably 0.2 to 2% by weight as a solid content on the basis of the fiber weight.

Glycerin may be applied not only to the top sheet of the disposable wearing article but also to a second sheet and an absorber. As this application method, the same method as the application method to the top sheet can be adopted.

<Sensory Effect Confirmation Test by Application of Glycerin>

Various characteristics such as an average friction coefficient MIU, a surface water ratio, and a water activity value were measured for samples of various top sheets illustrated in Table 1. The glycerin content was measured by the measurement method described above. Each of samples 1 to 10 was a nonwoven fabric with or without a hydrophilic lotion applied before being assembled into a product, and each of samples 11 to 15 was a top sheet removed from a commercial product. In addition, a surface of each of the top sheets was stroked in the front-back direction with a hand, and smoothness and moist feeling were evaluated in three stages (⊙ . . . very good, Δ . . . better than sample 5, × . . . about the same) as compared with sample 5.

TABLE 1

| Sample No. | | 1 | 2 | 3 | 4 | 5 |
|---|---|---|---|---|---|---|
| Top sheet | Fineness (dtex) | 2.0/2.2 (PE•PET) | 2.0/2.2 (PE•PET) | 2.0/2.2 (PE•PET) | 2.0/2.2 (PE•PET) | 2.0/2.2 (PE•PET) |
| | Basis weight (g/m²) | 25 | 20 | 20 | 20 | 20 |
| | Thickness (mm) | 1.1 | 0.9 | 0.9 | 0.6 | 0.6 |
| | Fiber material | PE/PET(mixed) | PE/PET(mixed) | PE/PET(mixed) | PE/PET(mixed) | PE/PET(mixed) |
| | Fiber bonding method | Thermal bond | Thermal bond | Thermal bond | Thermal bond | Thermal bond |

TABLE 1-continued

| Sample No. | | 1 | 2 | 3 | 4 | 5 |
|---|---|---|---|---|---|---|
| Glycerin-containing region | Arrangement | Longitudinal stripe | Longitudinal stripe | Longitudinal stripe | Longitudinal stripe | Longitudinal stripe |
| | MD size (mm) | 200 | 200 | 200 | 200 | — |
| | CD size (mm) | 5 | 5 | 5 | 5 | — |
| | Number (interval 32x) | 4 (5) | 4 (5) | 4 (10) | 4 (5) | — |
| Content of glycerin | (g/m²) | 1.7 | 1.3 | 1.4 | 1.1 | 0 |
| Composition of lotion | Glycerin | 80 | 80 | 80 | 80 | — |
| | Water | 20 | 20 | 20 | 20 | — |
| Application amount of lotion | (g/m²) | 8.5 | 8.5 | 8.5 | 8.5 | 0 |
| Viscosity of lotion (Pa · s) 20° C. | | 372 | 372 | 372 | 372 | — |
| Average friction coefficient MIU | | 0.33 | 0.34 | 0.34 | 0.33 | 0.37 |
| Variation deviation of average friction coefficient MMD | | 0.01 | 0.01 | 0.01 | 0.01 | 0.01 |
| Surface water ratio (%) | | 5.6 | 5.6 | 5.6 | 5.6 | 0.3 |
| Smoothness | | ⊙ | ⊙ | ⊙ | ⊙ | — |
| Moist feeling | | ⊙ | ⊙ | ⊙ | ⊙ | — |

TABLE 2

| Sample No. | | 6 | 7 | 8 | 9 | 10 |
|---|---|---|---|---|---|---|
| Top sheet | Fineness (dtex) | 2.0/2.2 (PE•PET) | 2.0/2.2 (PE•PET) | 2.0/2.2 (PE•PET) | 2.0/2.2 (PE•PET) | 2.0/2.2 (PE•PET) |
| | Basis weight (g/m²) | 20 | 20 | 20 | 20 | 20 |
| | Thickness (mm) | 0.6 | 0.6 | 0.6 | 0.6 | 0.6 |
| | Fiber material | PE/PET(mixed) | PE/PET(mixed) | PE/PET(mixed) | PE/PET(mixed) | PE/PET(two-layered product) |
| | Fiber bonding method | Thermal bond | Thermal bond | Thermal bond | Thermal bond | Thermal bond |
| Glycerin-containing region | Arrangement | Longitudinal stripe | Longitudinal stripe | Longitudinal stripe | Longitudinal stripe | Longitudinal stripe |
| | MD size (mm) | 200 | 200 | 200 | 200 | 200 |
| | CD size (mm) | 5 | 5 | 5 | 5 | 5 |
| | Number (interval 32x) | 4 (5) | 4 (5) | 4 (5) | 4 (5) | 4 (5) |
| Content of glycerin | (g/m²) | 0.50 | 0.70 | 2.6 | 2.8 | 1.2 |
| Composition of lotion | Glycerin | 80 | 80 | 80 | 80 | 80 |
| | Water | 20 | 20 | 20 | 20 | 20 |
| Application amount of lotion | (g/m²) | 3.5 | 5.0 | 15.0 | 17.6 | 8.5 |
| Viscosity of lotion (Pa · s) 20° C. | | 372 | 372 | 372 | 372 | 372 |
| Average friction coefficient MIU | | 0.41 | 0.40 | 0.30 | 0.30 | 0.51 |
| Variation deviation of average friction coefficient MMD | | 0.01 | 0.01 | 0.01 | 0.01 | 0.01 |
| Surface water ratio (%) | | 3.0 | 4.2 | 8.0 | 8.9 | 3.0 |
| Smoothness | | ○ | ○ | ⊙ | ⊙ | Δ |
| Moist feeling | | ○ | ○ | ⊙ | ⊙ | Δ |

TABLE 3

| Sample No. | | 11 | 12 | 13 | 14 | 15 |
|---|---|---|---|---|---|---|
| Top sheet | Fineness (dtex) | Manufacturer A commercially available diaper (1) | Manufacturer B commercially available diaper (1) | Manufacturer A commercially available diaper (2) | Manufacturer B commercially available diaper (2) | Manufacturer C commercially available diaper |
| | Basis weight (g/m²) | | | | | |
| | Thickness (mm) | | | | | |
| | Fiber material | | | | | |
| | Fiber bonding method | | | | | |

TABLE 3-continued

| Sample No. | | 11 | 12 | 13 | 14 | 15 |
|---|---|---|---|---|---|---|
| Glycerin-containing region | Arrangement | — | — | — | — | — |
| | MD size (mm) | — | — | — | — | — |
| | CD size (mm) | — | — | — | — | — |
| | Number (interval 32x) | — | — | — | — | — |
| Content of glycerin | $(g/m^2)$ | — | — | — | — | — |
| Composition of lotion | Glycerin | — | — | — | — | — |
| | Water | — | — | — | — | — |
| Application amount of lotion | $(g/m^2)$ | — | — | — | — | — |
| Viscosity of lotion (Pa · s) 20° C. | | — | — | — | — | — |
| Average friction coefficient MIU | | 0.65 | 0.62 | 0.48 | 0.69 | 0.58 |
| Variation deviation of average friction coefficient MMD | | 0.01 | 0.01 | 0.01 | 0.01 | 0.01 |
| Surface water ratio (%) | | 0.3 | 0.1 | 0.2 | 0.3 | 0.3 |
| Smoothness | | X | X | Δ | X | X |
| Moist feeling | | X | X | X | X | X |

As illustrated in Table 1 to 3, it was found that the surfaces of the top sheets of samples 1 to 4 and 6 to 9, particularly samples 1 to 4, 8, and 9 provided very smooth feeling and moist feeling. Samples 10 to 15 were inferior in smoothness and moist feeling to these samples. Note that sample 9 was moist but had a sticky texture.

<Measurement of Transepidermal Water Loss (TEWL) and Horny Layer Water Content>

A transepidermal water loss (TEWL) and a horny layer water content after the top sheet was brought into contact with a skin of a subject (each of two males and one female in thirties) for one hour were measured by the following procedure. For the measurement of TEWL, a portable water transpiration meter SWL-5001 manufactured by Delfin Technologies was used. For the measurement of the honey layer water content, a skin horny layer water content measuring apparatus SKICON-200EX-USB manufactured by YAYOI Co., Ltd. was used.

(1) A top sheet of sample 1 in Table 1, a top sheet of sample 11 in Table 3, a top sheet of sample 14 in Table 3, and a top sheet of sample 15 in Table 3 were prepared, and each of the samples was cut into a 2 cm square to prepare a test piece. Note that, for the test piece of sample 1, the test piece was cut such that the glycerin-containing region passed through the center.

(2) Measurement points were marked on both arms of a subject at positions 8 cm, 11 cm, 14 cm, and 17 cm from the wrist (eight measurement points in total per person and 24 measurement points for all the subjects).

(3) About 0.1 g of fluff pulp was allowed to stand at each of the measurement points, 1 ml of an alkali aqueous solution (0.1 M NaCO₃aq.) was added dropwise to the fluff pulp, a food wrap film was wound therearound and fixed thereon, and the food wrap film and the fluff pulp were allowed to stand for one hour.

(4) After being allowed to stand for one hour, the food wrap film and the fluff pulp were removed, and each of the measurement points was lightly wiped with a test paper rag.

(5) The measurement points were dried for 15 minutes. Thereafter, the test piece was placed on each of the measurement points, fixed with a cellophane pressure sensitive adhesive tape, and left in this state for one hour.

(6) After being left for one hour, the sample was removed, and TEWL was measured three times for each of the measurement points. An average value of all the measured values for all the subjects was taken as a measurement result of TEWL. After the measurement of TEWL, a horny layer water content was measured three times at each of the measurement points, and an average value of all the measured values of all the subjects was taken as a measurement result of the horny layer water content.

Figure 13:
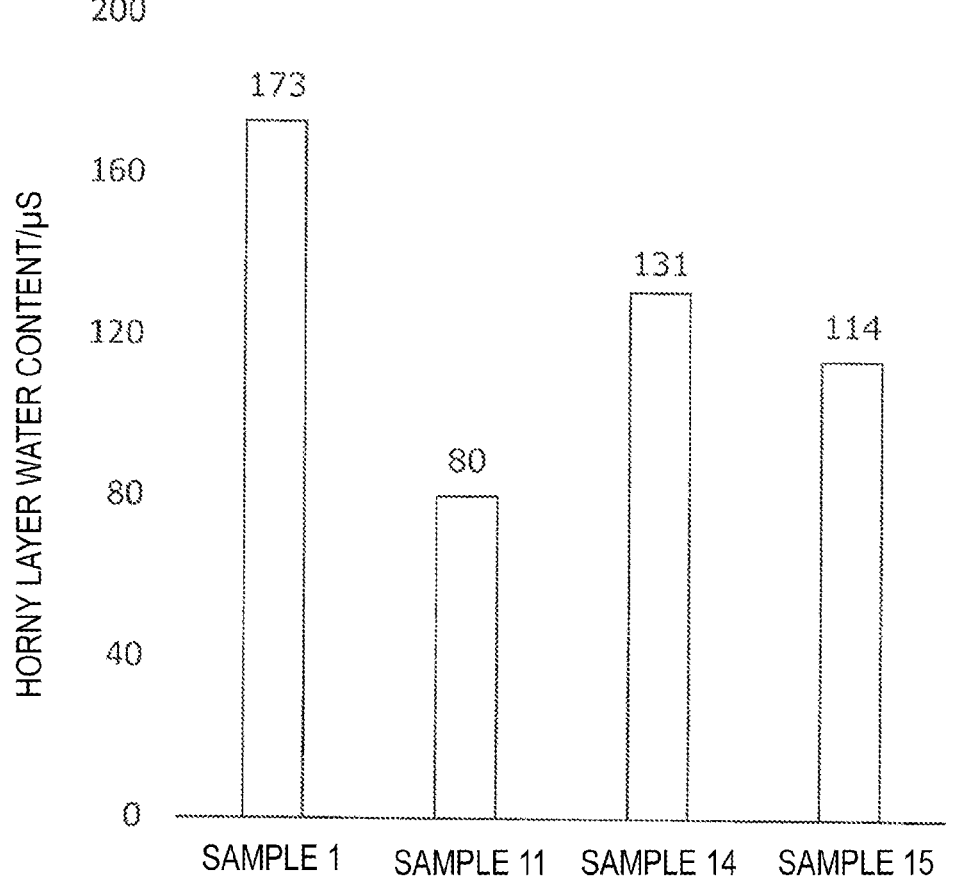
FIG. 13 is a graph illustrating measurement results of a horny layer water content.
Figure 14:
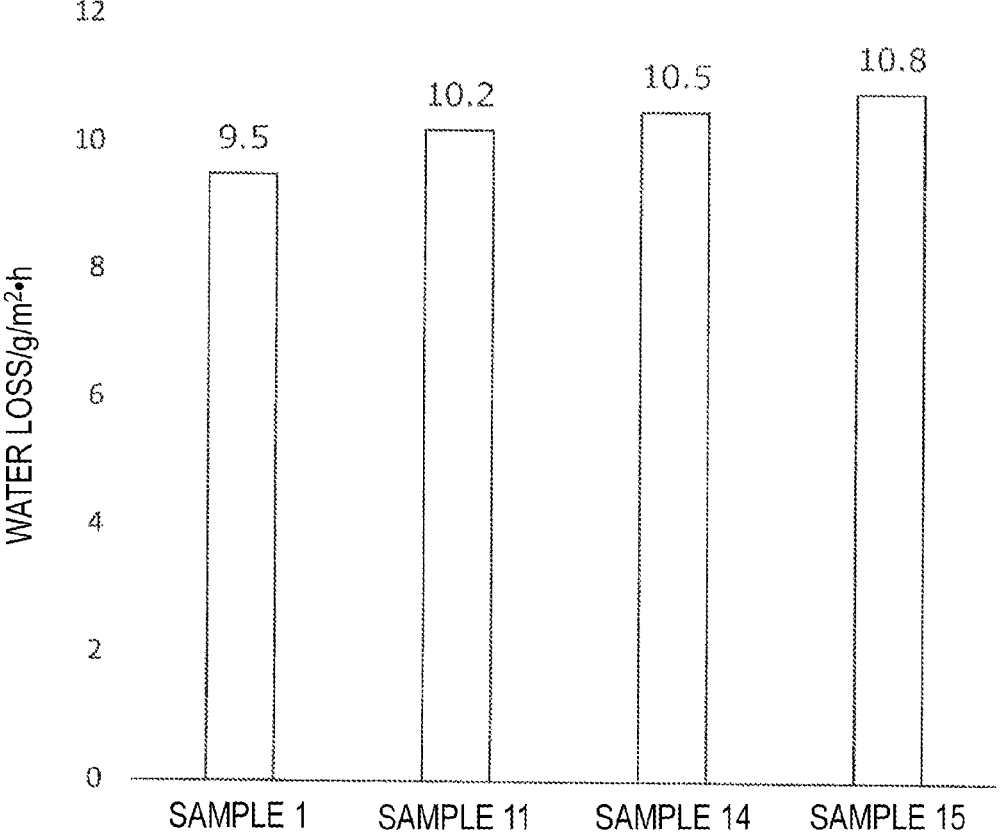
FIG. 14 is a graph illustrating measurement results of a transepidermal water loss (TEWL).

A comparative graph of the measurement results of the horny layer water content is illustrated in FIG. 13. A comparative graph of the measurement results of TEWL is illustrated in FIG. 14. From these measurement results, it has been found that, in a case of using the top sheet (containing glycerin) of sample 1 having a glycerin-containing region, water in a skin is less likely to escape to the outside and the water amount of the skin is larger as compared with a case of using another top sheet not containing glycerin.

<Skin Observation Test by Doctor>

A sample diaper having a substantially similar structure to the tape-type disposable diaper illustrated in FIGS. 1 to 5 and 10 and including the top sheet (containing glycerin) of sample 1 in Table 1 was manufactured. The sample diaper was continuously used for one week by a subject, and a condition of a skin was observed by a doctor immediately before and immediately after use. Note that, as the subject, 33 healthy infants from six months to one year old who were using a tape-type disposable diaper (including a top sheet not containing glycerin) were used.

As a result of observation of findings by a doctor, it was confirmed that no problematic skin symptoms were observed after the test, and six out of seven subjects with erythema confirmed by observation before the test tended to improve erythema.

<Measurement of IL-1α Secretion Amount>

Using a three-dimensional cultured skin model (immature model), an influence of the top sheet on IL-1α production was evaluated as follows.

As the three-dimensional cultured skin model, SkinEthic RHE-D7 (EPISKIN, hereinafter referred to as RHE) was used, and acclimatized and cultured for two hours in a 24 well plate using Growth medium (EPISKIN).

A top sheet similar to that of sample 1 in Table 1 was prepared, and cut along a surface shape (circle having a diameter of 8 mm) of RHE to prepare a blank test piece. Thereafter, a hydrophilic lotion was applied to an entire surface of the blank test piece with a similar composition and application amount to those of sample 1 in Table 1 to prepare a glycerin-containing test piece.

The test piece was directly placed on a surface of the cultured RHE, acclimatized, and incubated for 72 hours. 24 hours after the test piece was placed on the RHE, the test piece was removed. The medium and the test piece were replaced with a fresh growth medium and a test piece, respectively, and continuous culture was performed. The medium was collected, and the IL-1α secretion amount on Day 1 was measured by an ELISA method. After 24 hours further elapses (48 hours in total elapses), the test piece was removed. The medium and the test piece were replaced with a fresh growth medium and a test piece, respectively, and continuous culture was performed. The medium was collected. The IL-1α secretion amount on Day 2 was measured by a similar operation to Day 1. After 24 hours further elapses (72 hours in total elapses), the test piece was removed, and the medium was collected. The IL-1α secretion amount on Day 3 was measured by a similar operation to Day 1. In addition, the RHE was collected and subjected to measurement of a filaggrin amount described later.

In a case where nothing was placed on the surface of the RHE (control), the IL-1α secretion amount was measured and the RHE was collected similarly.

The IL-1α secretion amount was measured by quantifying IL-1α in the medium by sandwich ELISA using an anti-IL-1α antibody, HumanIL-1α/IL-1 F1 Antibody (MAB200) (R&D systems, Inc.) diluted to an appropriate concentration as a capture antibody and using a biotin-labeled anti-IL-1α antibody, HumanIL-1α/IL-1 F 1 Biotinylated Antibody (BAF200) (R&D systems, Inc.) as a detection antibody. Details thereof are as follows. That is, the collected medium diluted to a predetermined concentration was added to a plate coated with the capture antibody and incubated, and then the detection antibody was added thereto. Steptavidin-HRP (DY998) (R&D systems, Inc.) was added thereto to cause a reaction, then a substrate solution (DY999) (R&D systems, Inc.) was added thereto to cause a reaction, the reaction was stopped by Stop solution (DY994) (R&D systems, Inc.), and then absorbance at 450 nm was measured.

Figure 15:
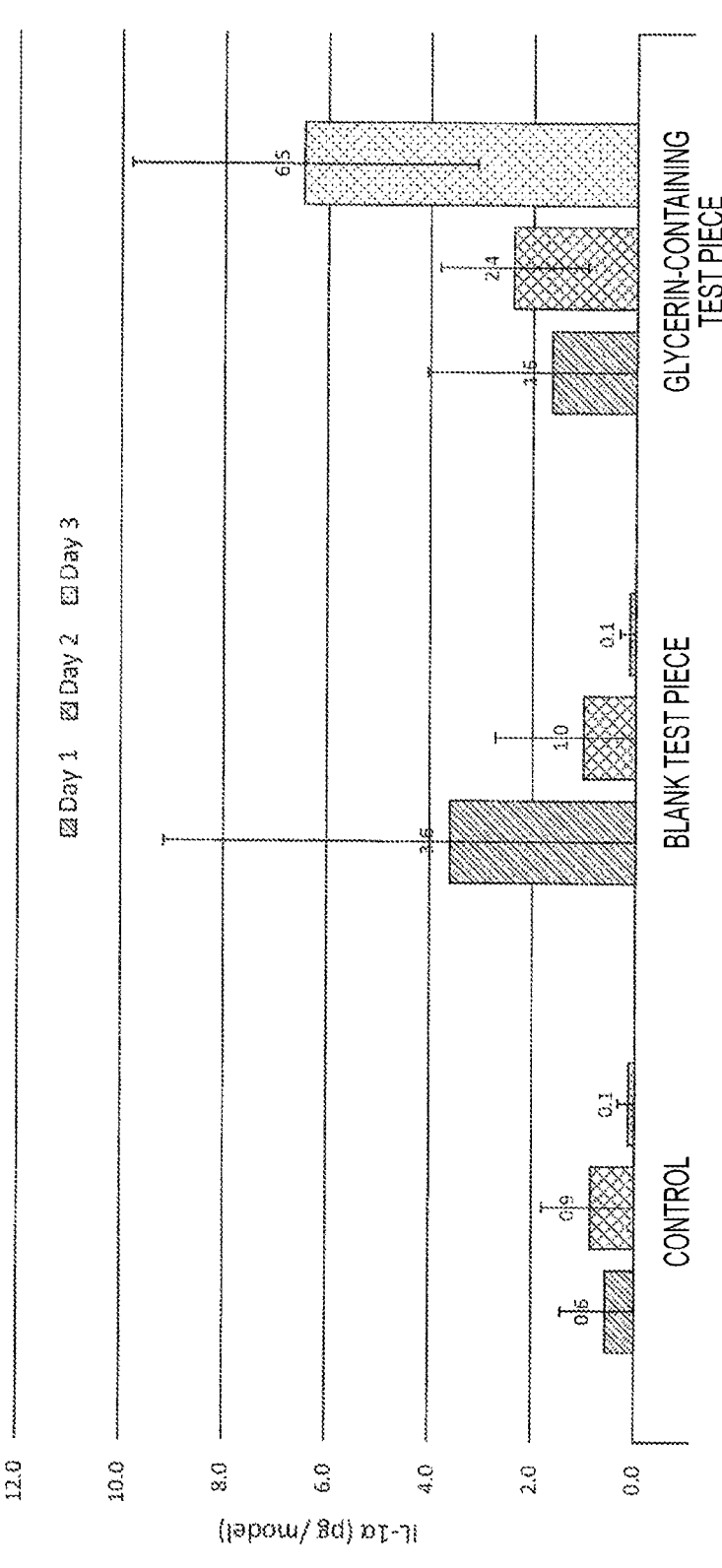
FIG. 15 is a graph illustrating a measurement result of an IL-1α secretion amount.

An IL-1α amount in a model having an IL-1α amount below a detection limit was regarded as 0, and the total IL-1α amount from Day 1 to Day 3 was 10.5±4.9 (pg/model) when the blank test piece was used, whereas the total IL-1α amount from Day 1 to Day 3 was 4.7±7.5 (pg/model), which is ½ or less of the above value, when the glycerin-containing test piece was used, as illustrated in FIG. 15.

<Measurement of Filaggrin Amount>

Using a three-dimensional cultured skin model (immature model), an influence of the top sheet on a filaggrin amount was evaluated as follows.

A 5 μm-thick section was prepared using a frozen block in which the RHE collected in the measurement of the IL-1α secretion amount was embedded in an O.C.T. compound. The section was attached to slide glass and then air-dried. The section was fixed at room temperature for 15 minutes using PBS (−) containing 4% paraformaldehyde, blocked for one hour at room temperature using PBS (−) containing 1% bovine serum albumin (BSA), and then caused to react with an anti-filaggrin antibody (GeneTex) at 40° C. overnight. As a secondary antibody, an anti-mouse IgG AlexaFluor 488 (Cell Signaling Technologies) was caused to react at room temperature for two hours. As counterstaining, cell nuclei were stained with Hoechst 33342 (Cell Signaling Technologies) and encapsulated with Marinol (MUTO CHEMICAL CO., LTD.). Thereafter, fluorescence of green (filaggrin) and blue (cell nuclei) in a tissue was observed using a fluorescence microscope.

Figure 16:
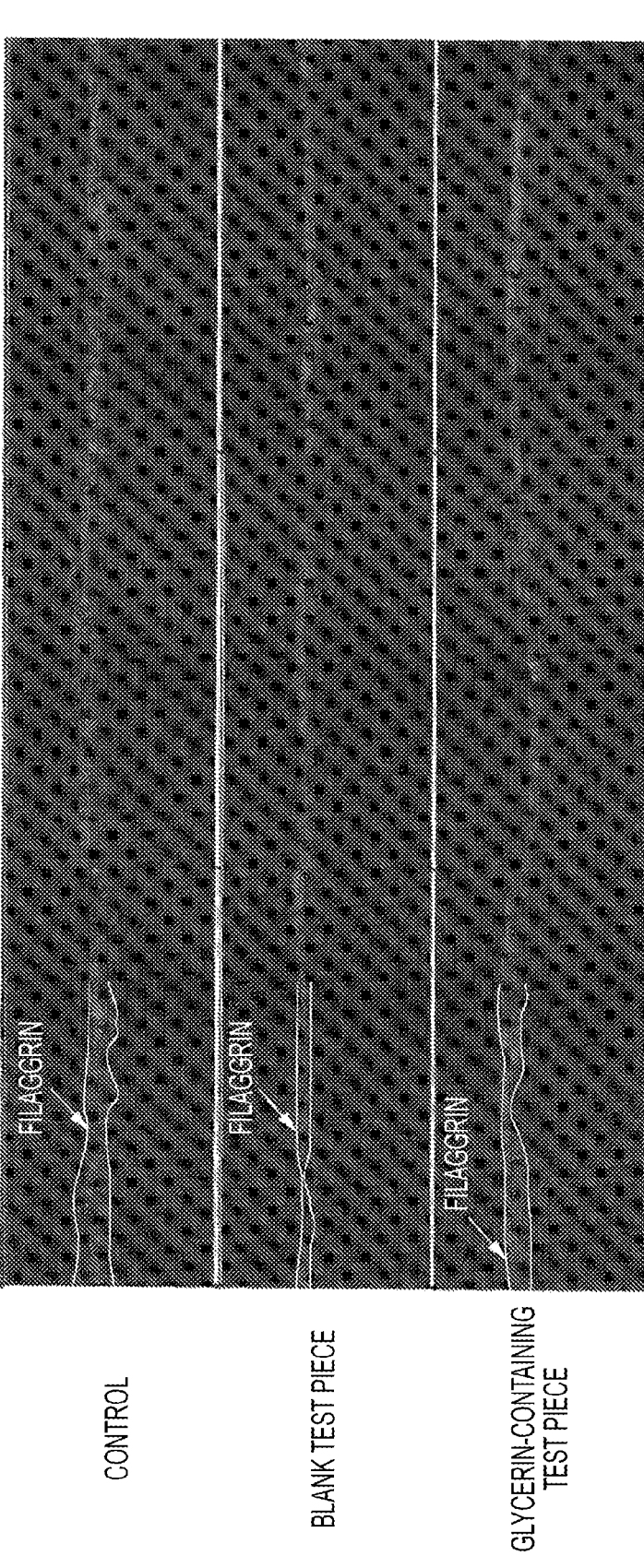
FIG. 16 is a photograph illustrating an observation result of a filaggrin amount.

As a result of the observation, as illustrated in FIG. 16, in the case of the control, expression of filaggrin was observed in the entire horny layer. In addition, in a case where the blank test piece was placed on a surface of the horny layer, expression of filaggrin was reduced as compared with the case of the control. Meanwhile, it was found that in a case where the glycerin-containing test piece was placed on the surface of the horny layer, the decrease in filaggrin expression was suppressed as compared with the case where the blank test piece was placed.

[Experiment by Application of Body Fluid Pervious Treatment Agent]

Various treatment agents were used as the body fluid pervious treatment agent. According to the type of the treatment agent, for each of a top sheet alone and a simulated disposable diaper in which a top sheet, an intermediate sheet, an absorber, and a back sheet were disposed in this order, tests were performed regarding an absorption speed, a returning amount, and a flow (diffusion) distance in a case where simulated loose stool (yogurt) was applied.

<Type and Adjustment of Top Sheet>

As the body fluid pervious treatment agent, various treatment agents having different HLB values were prepared.

(1) 1 g of a treatment agent was applied to 1 g of a commercially available A4 size nonwoven fabric (mixed air through nonwoven fabric of 2.0 dtex PE fibers+2.2 dtex PET fibers), and the treatment agent was diluted with ionic water so as to have a concentration of 0.1% by weight. Note that the term "% by weight" as used herein refers to an attachment amount ratio of the treatment agent per fiber weight of the nonwoven fabric.

(2) 0.5 g of the treatment agent is put in a tray, and the top sheet is stretched and immersed therein from a back surface side for 30 seconds, then returned to a front surface side of the top sheet, and similarly, 0.5 g is immersed therein for 30 seconds.

(3) The top sheet is dried overnight.

(4) In a concentration gradient test of the treatment agent, the top sheet is stretched and immersed from a back surface side for 30 seconds and then returned to a front surface side of the top sheet, and the front surface is immersed in the treatment agent having a concentration different from that for the back surface for 30 seconds.

<Test on Top Sheet Alone>

As simulated feces, 5 cc of 65% commercially available yogurt (ionic water:yogurt=7:13) is prepared with ionic water. A trace amount of blue dye was added thereto to make the simulated feces visible.

(1) As a back absorber, two sheets of "Pro-wipestrong type" having a basis weight of 80 g/m², manufactured by Daio Paper Mfg. Co., Ltd. are laid, and each of various top sheets is placed thereon. 10 cc of the simulated feces is injected thereinto at a speed of 120 ml/min. Time until the liquid disappears from a surface of the top sheet is measured and taken as an absorption speed.

(2) Three minutes after the injection, 10 sheets of filter paper and 1 kg of cylindrical weight (area: 100 cm²) are placed on the injection location.

(3) One minute after the placement, the weight of the filter paper is measured, and a value obtained by subtraction is taken as the returning amount of the simulated feces.

(4) 15° liquid flow (diffusion distance and diffusion speed)

In a state where an upper side of a support plate of the top sheet was inclined at 15 degrees, the above injection test was performed and the absorption speed was measured. In addition, the diffusion length (maximum length) of the simulated feces on a surface of the top sheet after the simulated feces completely flowed through the surface was measured with a scale.

Tables 4 and 5 illustrate results thereof.

TABLE 4

| Surfactant | None | S1 | S2 | S3 | S4 |
|---|---|---|---|---|---|
| HLB | — | 1.5 | 14 | 12.5 | 17 |
| Concentration | — | 0.1% by weight | 0.1% by weight | 0.1% by weight | 0.1% by weight |
| Absorption speed (second) | 71 | 80 | 62 | 65 | 68 |
| Returning amount (g) | 0.47 | 0.53 | 0.47 | 0.48 | 0.51 |
| Flowing distance at 15 degrees in MD direction (mm) | 114 | 127 | 110 | 101 | 110 |

TABLE 5

| Surfactant | S3 | S3 | S3 | S3 | S3/S3 |
|---|---|---|---|---|---|
| HLB | 12.5 | 12.5 | 12.5 | 12.5 | 12.5/12.5 |
| Concentration | 0.10% by weight | 0.15% by weight | 0.2% by weight | 0.3% by weight | 0.1/0.2 |
| Absorption speed (second) | 65 | 73 | 68 | 70 | 71 |
| Returning amount (g) | 0.80 | 0.75 | 0.85 | 0.64 | 0.70 |
| Flowing distance at 15 degrees in MD direction (mm) | 109 | 115 | 111 | 116 | 111 |
| Absorption speed at 15 degrees in MD direction (second) | 27 | 26 | 28 | 26 | 27 |

<Evaluation of Results of Test with Top Sheet Alone>

(1) As illustrated in Table 4, due to a difference in HLB (difference in hydrophilicity/hydrophobicity), an S2 treatment agent (silicon-based) and an S3 treatment agent, which had an intermediate hydrophilic/hydrophobic degree and a good balance, had suitable absorption speeds and liquid flows (short diffusion distances).

It has been clarified that neither an S1 treatment agent (natural oil) having strong lipophilicity nor an S4 treatment agent (anionic surfactant) having strong hydrophilicity can be expected to have a desired effect.

In particular, the fatty acid alkanolamide (nonionic surfactant) S3 treatment agent was favorable, had good initial absorbency and diffusibility, and made it difficult for the simulated feces to flow (diffuse).

(2) As illustrated in Table 5, the effect did not change even when the concentration of the S3 treatment agent was increased. Note that the test date was different from that for the top sheet alone, the type of commercially available yogurt used was the same as that for the top sheet alone, but the properties thereof were different from that for the top sheet alone.

(3) As illustrated in Table 5, a gradient was given to the concentration on a back surface side and the concentration on a front surface side of the S3 treatment agent having an intermediate hydrophilic/hydrophobic degree and a good balance, but an effect thereof was not observed.

<Glycerin Application Test after Application of Body Fluid Pervious Treatment Agent>

A lotion (glycerin) was applied under the same condition to a top sheet (nonwoven fabric of the above sample No. 2) to which the fatty acid alkanolamide (nonionic surfactant) S3 treatment agent exhibiting favorable results was applied.

In addition, a top sheet to which a treatment agent was not applied, a top sheet to which only the lotion (glycerin) was applied, and a top sheet to which the S1 treatment agent having strong lipophilicity was applied were compared.

Table 6 illustrates results thereof.

TABLE 6

| Surfactant | — | — | S3 | S3 | S1 |
|---|---|---|---|---|---|
| HLB | — | — | 12.5 | 12.5 | 1.5 |
| Concentration | — | — | 0.1% by weight | 0.1% by weight | 0.1% by weight |
| Glycerin | — | 0.1% by weight | 0.1% by weight | 46% by weight | 0.1% by weight |
| Absorption speed (second) | 71 | 81 | 68 | 86 | 86 |
| Returning amount (g) | 0.75 | 0.48 | 0.77 | 0.66 | 0.61 |
| Flowing distance at 15 degrees in MD direction (mm) | 117 | 130 | 112 | 129 | 144 |
| Absorption speed at 15 degrees in MD direction (second) | 25 | — | 24 | 32 | — |

<Evaluation of Results of Glycerin Application Test>

(1) The top sheet to which the lotion (glycerin) is applied has a longer flow distance than the top sheet to which the lotion (glycerin) is not applied. It is considered that this is because the lotion (glycerin) reduces an ability of oils contained in feces to permeate the top sheet, and oils are repelled on a surface of the top sheet.

(2) The top sheet to which the S1 treatment agent having strong lipophilicity is applied and the lotion (glycerin) is applied has a significantly longer flow distance. It is considered that this is because water contained in feces is repelled by S1 on a lipophilic surface of the top sheet.

<Test on Simulated Disposable Diaper>

A similar test was performed on a simulated disposable diaper of a neonatal size in which a top sheet, an intermediate sheet, an absorber, and a back sheet were disposed in this order.

As simulated feces, 40% commercially available yogurt (ionic water:yogurt=3:2) is prepared. A trace amount of blue dye was added thereto to make the simulated feces visible.

(1) 10 cc of the simulated feces is injected into the simulated disposable diaper at a speed of 120 ml/min. Time until the liquid disappears from a surface of the top sheet is measured and taken as an absorption speed.

(2) Three minutes after the injection, 10 sheets of filter paper and 1 kg of cylindrical weight (area: 100 cm$^2$) are placed on the injection location.

(3) One minute after the placement, the weight of the filter paper is measured, and a value obtained by subtraction is taken as the returning amount of the simulated feces.

(4) 15° liquid flow (diffusion distance and diffusion speed)

In a state where an upper side of a support plate of the top sheet was inclined at 15 degrees with a downward gradient, 5 ml of the simulated feces was injected at a speed of 420 ml/min and a distance by which the simulated feces flowed on a surface was measured with a scale.

Note that the type of commercially available yogurt used was the same as that used in the test for the top sheet alone, but the properties thereof were different from that used in the test for the top sheet alone. The yogurt having a concentration of 40% was used, which was also different from that for the top sheet alone.

Table 7 illustrates results thereof.

TABLE 7

| Surfactant | None | S3 |
|---|---|---|
| HLB | — | 12.5 |
| Concentration | — | 0.1% by weight |
| Absorption speed (second) | 60 | 49 |
| Diffusion distance MD (mm) | 88 | 81 |
| Diffusion distance CD (mm) | 71 | 57 |
| Diffusion area MD × CD (mm2) | 0.0063 | 0.0046 |
| Returning amount (g) | 0.70 | 0.55 |
| Flowing distance at 15 degrees in MD direction (mm) | 238 | 180 |

<Evaluation of Results of Test with Simulated Disposable Diaper>

It has been clarified that application of the fatty acid alkanolamide (nonionic surfactant) treatment agent improves absorbability of a body fluid.

Embodiments include the following aspects.

<First Aspect>

A disposable wearing article including:

a top sheet having a skin contact region in contact with a skin of a wearer, wherein the top sheet is a nonwoven fabric having a fineness of 1 to 3 dtex and a basis weight of 10 to 30 $g/m^2$, and the skin contact region has a glycerin-containing region containing 0.7 to 2.7 $g/m^2$ of glycerin.

(Action and Effect)

The present disposable wearing article is characterized in that, in a combination of glycerin and a top sheet of a nonwoven fabric, the content of glycerin per unit area and a nonwoven fabric of fine fibers are combined and adopted as the top sheet. In such a top sheet, the fineness of fibers contributes to reduction of friction on a surface, and a friction reducing effect as a whole is improved together with a friction reducing effect by glycerin. In addition, retention of glycerin is also improved due to the fineness of fibers, and this also improves the friction reducing effect. Furthermore, glycerin contained in the top sheet is transferred to a skin of a wearer, and the skin of the wearer can be thereby moisturized (prevented from being dried) (particularly by permeation of glycerin into a horny layer). Therefore, in the present disposable wearing article, a physical irritation reducing action on a skin of a wearer and a moisturizing action on the skin of the wearer are highly compatible, and in particular, an excellent rash preventing effect can be obtained.

<Second Aspect>

The disposable wearing article according to the first aspect, wherein the glycerin-containing region has a size in the MD direction of 5 mm or more and a size in the CD direction of 5 mm or more, and an area ratio of the glycerin-containing region in the skin contact region in an unfolded state is 3% or more.

(Action and Effect)

When the size and area ratio of the glycerin-containing region are within the above ranges, a physical irritation reducing action and a moisturizing action on a skin of a wearer are particularly excellent.

<Third Aspect>

The disposable wearing article according to the first or second aspect, wherein an IL-1α secretion amount measured by bringing the glycerin-containing region of the top sheet into contact with a three-dimensional cultured skin model is ½ or less of that of a sheet that is different only in that the sheet does not contain glycerin.

(Action and Effect)

The IL-1α (interleukin-1α) is an inflammatory cytokine produced in a skin when the skin receives stimulation to cause rash (skin redness). That is, when the IL-1α secretion amount measured by bringing the glycerin-containing region of the top sheet into contact with the three-dimensional cultured skin model is as small as in the present aspect, an excellent rash preventing property can be obtained. Note that a method for measuring the IL-1α secretion amount is as described above.

<Fourth Aspect>

The disposable wearing article according to any one of the first to third aspects, wherein a filaggrin amount measured by bringing the glycerin-containing region of the top sheet into contact with a three-dimensional cultured skin model is larger than that of a sheet that is different only in that the sheet does not contain glycerin.

(Action and Effect)

Filaggrin is one of the main components of honey layer, and it is known that filaggrin largely affects the strength and flexibility of the horny layer, and when the amount of filaggrin is small, horny layer cells are easily peeled off, and a transepidermal water loss (TEWL) also increases. In addition, filaggrin becomes a natural moisturizing factor (NMF) by decomposition, and also plays a role of moisturizing the horny layer and maintaining a pH. That is, when the filaggrin amount measured by bringing the glycerin-containing region of the top sheet into contact with the three-dimensional cultured skin model is as large as in the present aspect, an excellent rash preventing property can be obtained. Note that a method for measuring the filaggrin amount is as described above.

<Fifth Aspect>

The disposable wearing article according to any one of the first to fourth aspects, wherein the nonwoven fabric is a nonwoven fabric of hydrophilic fibers in which a hydrophilizing agent is applied to fibers of a hydrophobic resin.

(Action and Effect)

As the nonwoven fabric of the top sheet, a nonwoven fabric using fibers of a hydrophobic resin is preferable because of low cost. However, the nonwoven fabric using fibers of a hydrophobic resin itself has poor retention of glycerin. Therefore, in this case, it is preferable to use a nonwoven fabric of hydrophilic fibers using a hydrophilizing agent to enhance the retention of glycerin in the nonwoven fabric.

EXPLANATION OF TERMS IN SPECIFICATION

The following terms in the specification have the following meanings unless otherwise specified in the specification.

"Front-back direction" means a direction (longitudinal direction) indicated by a reference character LD in the drawing, "width direction" means a direction (left-right direction) indicated by a reference character WD in the drawing, and the front-back direction and the width direction are orthogonal to each other.

"MD (Machine Direction) direction" and the "CD (Cross Direction) direction" mean a flow direction (MD direction) in a manufacturing facility and a lateral direction (CD direction) orthogonal thereto, respectively, one of which is a front-back direction and the other is a width direction depending on a part of a product. The MD direction of a nonwoven fabric is a direction of fiber orientation of the nonwoven fabric. The fiber orientation is a direction in which fibers of a nonwoven fabric are aligned, and can be determined by, for example, a measurement method in accordance with a fiber orientation test method based on zero distance tensile strength by the TAPPI standard method 1481 or a simple measurement method for determining a fiber orientation direction based on a tensile strength ratio in a front-back direction and a width direction.

"Front surface side" means a side closer to a wearer's skin when a diaper is worn. "Back surface side" means a side far from a wearer's skin when a diaper is worn.

"Front surface" means a surface closer to a wearer's skin when a diaper is worn. "Back surface" means a surface far from a wearer's skin when a diaper is worn.

"Area ratio" means the ratio of a target portion to a target region, and represents a ratio expressed by percentage, obtained by dividing the total area of a target portion (for example, holes) in a target region (for example, cover nonwoven fabric) by the area of the target region. In a form in which a large number of target portions are disposed at intervals, it is desirable to set the target region to a size that includes 10 or more target portions and to determine the area ratio. For example, the area ratio of a hole can be measured according to the following procedure using, for example, a trade name VHX-1000 manufactured by KEYENCE Corporation under measurement conditions of 20 times.

(1) A lens having a magnification of 20 is set to VHX-1000, and the focus is adjusted. The position of a nonwoven fabric is adjusted such that 4×6 holes are included.

(2) The brightness of the region of the holes is specified, and the area of the hole is measured.

(3) Color extraction of "Area measurement" in "Measurement/Comment" is clicked. The portion of the holes is clicked.

(4) "Collective measurement" is clicked, "Display measurement result window" is checked, and data is stored as CSV data.

"Stretch rate" means a value obtained when a natural length is 100%. For example, a stretch rate of 200% is synonymous with an elongation ratio of 2.

"Gel strength" is measured as follows. To 49.0 g of artificial urine (mixture of 2% by weight of urea, 0.8% by weight of sodium chloride, 0.03% by weight of calcium chloride dihydrate, 0.08% by weight of magnesium sulfate heptahydrate, and 97.09% by weight of deionized water), 1.0 g of a super absorbent polymer is added, and the resulting mixture is stirred with a stirrer. The gel thus generated is left in a thermohygrostat at 40° C.×60% RH for three hours. Thereafter, the temperature is returned to room temperature, and gel strength is measured with a curdmeter (Curdmeter-MAX ME-500 manufactured by I. Techno Engineering Co., Ltd.).

"Basis weight" is measured as follows. A sample or a test piece is predried and then left in a test chamber or an apparatus in a standard state (test location is at a temperature of 23±1° C. and a relative humidity of 50±2%) so as to have a constant weight. Predrying refers to causing a sample or a test piece to have a constant weight in an environment of a temperature of 100° C. Note that fibers having an official moisture regain of 0.0% do not have to be predried. A sample of 100 mm×100 mm in size is cut out from a test piece having a constant weight using a template for sampling (100 mm×100 mm). The weight of the sample is measured. The weight is multiplied by 100 to calculate the weight per square meter to be used as a basis weight.

"Thickness" is automatically measured under conditions that a load is 0.098 N/cm$^2$ and a pressing area is 2 cm$^2$ using an automatic thickness meter (KES-G5 handy compression measuring program). The thickness of a perforated nonwoven fabric is measured at a portion other than a hole and a protruding portion around the hole.

Water absorption capacity is measured in accordance with JIS K7223-1996 "Test method for water absorption capacity of super absorbent polymer".

Water absorption speed is "time to end point" when JIS K7224-1996 "Test method for water absorption speed of super absorbent polymer" is performed using 2 g of super absorbent polymer and 50 g of physiological saline.

"Unfolded state" means a flatly unfolded state without contraction or slackness.

The size of each portion means a size not in a natural length state but in an unfolded state unless otherwise specified.

"Melt viscosity" is measured at a specified temperature using a Brookfield B-type viscometer (spindle No. 027) in accordance with JIS Z 8803.

"Maximum size" of a hole means a longer one of the size in the MD direction and the size in the CD direction.

When "glycerin-containing region" can be visually identified, such as being colored, the shape thereof can be visually identified and the size thereof can be measured. Meanwhile, when the glycerin-containing region 32 cannot be visually identified, the glycerin-containing region 32 can be identified by an appropriate method.

For example, a required number of test pieces (for measurement and for position identification) having the same position of the glycerin-containing region 32 are prepared, the glycerin-containing region 32 in the top sheet 30 of the test piece for position identification is colored with an appropriate colorant in a color different from a surrounding portion, the coloring position is identified using a ruler or an appropriate image measuring apparatus, and then measurement can be performed using the same position as the coloring position identified by the test piece for position identification in the test piece for measurement as the glycerin-containing region 32. As an agent capable of coloring the glycerin-containing region 32, a water leakage color developing developer "MORAYMILLE W" manufactured by Taseto Co., Ltd. can be suitably used.

In addition, when the amount of water in the glycerin-containing region 32 is equal to or more than a certain value, by imaging a surface of the top sheet under illumination (indoor light and external light from a window) using a near infrared camera (NIRCam-640SN manufactured by Vision Sensing), the glycerin-containing region 32 is visualized (identified) as a darker portion than surroundings, and the size thereof can be measured.

"Average friction coefficient MIU" and "variation deviation of average friction coefficient MMD" each mean a value at a sensor moving distance of 20 mm, measured using a friction tester KES-SE (10 mm square silicon sensor, load 50 g) manufactured by Kato Tech Co., Ltd. A moving direction (friction direction) of the sensor is the MD direction of the top sheet. When a product is measured, members other than the top sheet in the product are removed or cut (therefore, for example, a member welded to the top sheet is not removed) within a range that does not affect a friction test of a surface of the top sheet, and the test is performed in an unfolded state.

Figure 12:
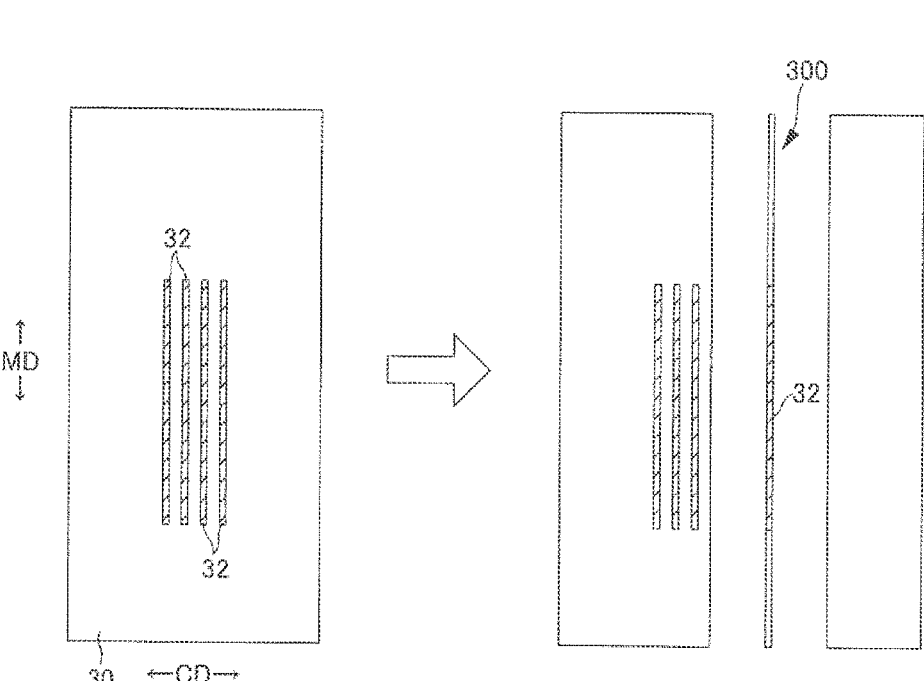
FIG. 12 is a plan view for explaining a test piece.
Figure 12:
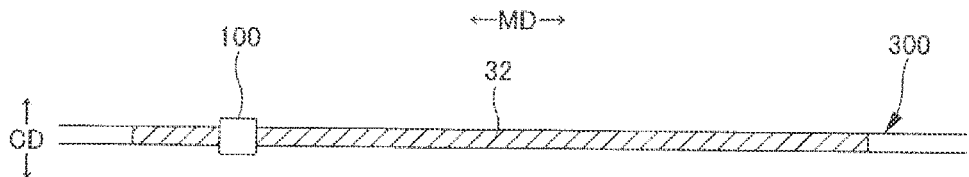

In addition, when the size in the CD direction of the glycerin-containing region in the top sheet is less than the size (10 mm) of the sensor, as illustrated in FIG. 12(*a*), the top sheet 30 is cut along a side edge of the glycerin-containing region 32 to prepare a test piece 300 (narrower than a sensor 100) including only the glycerin-containing region 32, and as illustrated in FIG. 12(*b*), the center of the sensor 100 is aligned with the center of the test piece 300 in the CD direction, and measurement is performed on this test piece. Note that, in each measurement, glycerin or the like attached to a surface of the sensor 100 is sufficiently wiped off, and then next measurement is performed.

Note that the glycerin-containing region 32 is identified by the above-described method.

"Surface water ratio" is an average value calculated by measuring arbitrary three points of the glycerin-containing region 32 using a moisture checker (MY-808S) manufactured by Scalar Corporation. Note that, in each measurement, glycerin or the like attached to a measurement surface of the moisture checker is sufficiently wiped off, and then next measurement is performed. Note that the glycerin-containing region 32 is identified by the above-described method.

"Water activity value" can be measured by an electric resistance type water activity measuring apparatus such as EZ-100ST (electric resistance type) manufactured by Freund Corporation. Before the measurement, calibration is performed using a saturated solution. The measurement can be performed in accordance with an electric resistance test based on the food hygiene inspection guidelines. That is, a sample having a volume of 3% or more of a detector internal space volume of a water activity measuring apparatus is collected, placed on an aluminum foil dish or an open flat dish, and immediately put in the detector. The detector is sealed and placed under a condition of 25±2 degrees. A numerical value is read at intervals of 10 minutes. A time point when no change in the numerical value is observed is regarded as a time point when a water vapor pressure in the detector reaches an equilibrium state, and a numerical value at that time point is taken as a measurement value of the sample. Each same sample is measured three times, and an average value of the three measured values is defined as a water activity value.

"Viscosity" is measured at a predetermined temperature using a Brookfield B-type viscometer (spindle No. 027) in accordance with JIS Z 8803.

When environmental conditions in a test and a measurement are not described, the test and the measurement are performed in a test room or an apparatus in a standard state (test location is at a temperature of 23±1° C. and a relative humidity of 50±2%).

INDUSTRIAL APPLICABILITY

The present invention can be used not only for an underpants-type disposable diaper and a tape-type disposable diaper but also for a general disposable wearing article such as a pad-type disposable diaper, a disposable swim suit, a diaper cover, or a sanitary napkin.

REFERENCE SIGNS LIST

11 Liquid impervious sheet
14 Hole
20 Exterior nonwoven fabric
30 Top sheet
32 Glycerin-containing region
40 Intermediate sheet
50 Absorbent element
56 Absorber
58 Wrapping sheet
60 Rising gather
62 Gather sheet
LD Front-back direction
WD Width direction

The invention claimed is:

1. A disposable wearing article comprising:
a top sheet having a skin contact region configured to contact a skin of a wearer,
wherein the top sheet is formed of a nonwoven fabric having a fineness of 1.5 to 2.5 dtx, a basis weight of 15 to 25 $g/m^2$, and a thickness of 0.4 to 1.4 mm,
the nonwoven fabric is a nonwoven fabric of hydrophilic fibers in which a hydrophilizing agent is applied to fibers of a hydrophobic resin,
the skin contact region has,
in a region into which a body fluid pervious treatment agent is attached, the body fluid pervious treatment agent comprising a nonionic surfactant consisting of a single fatty acid alkanolamide having an HLB value of 8 to 15, and the body fluid pervious treatment agent not containing an anionic surfactant, a cationic surfactant, or an amphoteric ion-based surfactant,
a glycerin-containing region to which a hydrophilic lotion containing 70 to 90% by weight of glycerin and 10 to 30% by weight of water is applied,
an attachment amount of the body fluid pervious treatment agent in the region in which the body fluid pervious treatment agent is attached is 0.05 to 2% by weight,
the glycerin-containing region in the region in which the body fluid pervious treatment agent is attached contains 0.7 to 2.7 $g/m^2$ of glycerin and has a size of 100 mm or more in an MD (Machine Direction) direction and a size of 5 mm or more in a CD (Cross Direction) direction and,
an area ratio of the glycerin-containing region in the skin contact region in an unfolded state is 3% or more.
2. The disposable wearing article according to claim 1,
wherein the top sheet is a perforated nonwoven fabric having a hole arrangement region in which holes penetrating the top sheet from a front surface to a back surface are arranged in a predetermined pattern, and the hole has an area of 0.25 to 4.00 $mm^2$ and an area ratio of 0.1 to 10%.

3. A method for manufacturing a disposable wearing article, including a top sheet having a skin contact region configured to contact a skin of a wearer, comprising:

using a nonwoven fabric having a fineness of 1.5 to 2.5 dtx, a basis weight of 15 to 25 $g/m^2$ and a thickness of 0.4 to 1.4 mm as the top sheet; wherein the nonwoven fabric is a nonwoven fabric of hydrophilic fibers in which a hydrophilizing agent is applied to fibers of a hydrophobic resin;

attaching a body fluid pervious treatment agent comprising a nonionic surfactant consisting only of a single fatty acid alkanolamide having an HLB value of 8 to 15, the body fluid pervious treatment agent not containing an anionic surfactant, a cationic surfactant, or an amphoteric ion-based surfactant;

forming a region attaching the body fluid pervious treatment agent in which an attachment amount of the body fluid pervious treatment agent is 0.05 to 2% by weight on the basis of a fiber weight of the top sheet;

applying a hydrophilic lotion containing 70 to 90% by weight of glycerin and 10 to 30% by weight of water, to the region attaching the body fluid pervious treatment agent; and forming a glycerin-containing region containing 0.7 to 2.7 $g/m^2$ of glycerin and having a size of 100 mm or more in an MD (Machine Direction) direction, a size of 5 mm or more in a CD (Cross Direction) direction, and an area ratio of the glycerin-containing region in the skin contact region in an unfolded state of 3% or more.

* * * * *